US008999347B2

(12) United States Patent
Cohen et al.

(10) Patent No.: US 8,999,347 B2
(45) Date of Patent: Apr. 7, 2015

(54) VACCINES FOR MALARIA

(75) Inventors: Joseph D Cohen, Rixensart (BE); Martine Marchand, Rixensart (BE)

(73) Assignee: GlaxoSmithKline Biologicals, SA, Rixensart (BE)

( * ) Notice: Subject to any disclaimer, the term of this patent is extended or adjusted under 35 U.S.C. 154(b) by 600 days.

(21) Appl. No.: 12/810,364

(22) PCT Filed: Dec. 22, 2008

(86) PCT No.: PCT/EP2008/068130
§ 371 (c)(1),
(2), (4) Date: Jun. 24, 2010

(87) PCT Pub. No.: WO2009/080803
PCT Pub. Date: Jul. 2, 2009

(65) Prior Publication Data
US 2010/0272788 A1 Oct. 28, 2010

Related U.S. Application Data

(60) Provisional application No. 61/016,522, filed on Dec. 24, 2007, provisional application No. 61/016,525, filed on Dec. 24, 2007.

(51) Int. Cl.
*A61K 39/015* (2006.01)
*C07K 14/445* (2006.01)
*C12N 7/00* (2006.01)
*A61K 39/00* (2006.01)

(52) U.S. Cl.
CPC ............. *C07K 14/445* (2013.01); *A61K 39/015* (2013.01); *C12N 7/00* (2013.01); *A61K 2039/5258* (2013.01); *A61K 2039/55555* (2013.01); *A61K 2039/55566* (2013.01); *A61K 2039/55572* (2013.01); *A61K 2039/55577* (2013.01); *A61K 2039/6075* (2013.01); *C07K 2319/40* (2013.01); *C12N 2730/10123* (2013.01)

(58) Field of Classification Search
CPC .................... A61K 2039/6075; A61K 39/015; A61K 2039/55555; A61K 2039/55566; A61K 2039/55572; A61K 2039/55577; A61K 2039/5258; A61K 47/24; A61K 47/28; A61K 47/36; A61K 9/1272; A61K 9/1277; A61K 9/19; C07K 14/445; C12N 7/00
USPC ........ 424/192.1, 450, 272.1; 435/254.2, 69.3, 435/320.1, 235.1; 530/350
See application file for complete search history.

(56) References Cited

U.S. PATENT DOCUMENTS

2010/0062028 A1* 3/2010 Cohen et al. ............... 424/272.1
2010/0150998 A1* 6/2010 Cohen et al. ................ 424/450

FOREIGN PATENT DOCUMENTS

| EP | 1 623 720 | 2/2006 |
|---|---|---|
| WO | WO93/10152 | 5/1993 |
| WO | WO 2006/088597 | 8/2006 |
| WO | WO 2007/003384 | 1/2007 |
| WO | WO 2008/009650 | 1/2008 |
| WO | WO 2008/009652 A2 | 1/2008 |

OTHER PUBLICATIONS

Stewart et al (Infection and immunity, May 2007, vol. 75, No. 5, pp. 2283-2290).*
Jolivet, et al., "Polyvalent synthetic vaccines: Relationship between T Epitopes and Immunogenicity", *Vaccine*, 8(1):35-40 (1990).
Vreden, et al., "Phase I clinical trial of a recombinant malaria vaccine consisting of the circumsporozoite repeat region of *Plasmodium falciparum* coupled to hepatitis B surface antigen", *American Journal of Tropical Medicine & Hygiene*, 45(5):533-538 (1991).
Heppner, et al., "Towards an RTS, S-based, multi-stage, multi-antigen vaccine against falciparum malaria: Progress at the Walter Reed Army Institute of Research", *Vaccine*, 23(17-18):2243-2250 (2005).
Australian Government Patent Examination Report No. 1 dated Nov. 22, 2012, Application No. 2008339969.

* cited by examiner

*Primary Examiner* — Padma V Baskar
(74) *Attorney, Agent, or Firm* — James T. Olesen; Jeffrey Sutton

(57) ABSTRACT

The present invention relates to a novel lipoprotein particle, methods for preparing and purifying the same, its use in medicine, particularly in the prevention of malarial infections, compositions/vaccines containing the particle or antibodies against the protein particle such as monoclonal or polyclonal antibodies and use of the same, particularly in therapy. Furthermore, particles with the specific ratio can be prepared by employing yeast, *Saccharomyces cerevisiae* or *Pichia pastoris*. In particular it relates to an immunogenic protein particle comprising the following monomers:
  a. a fusion protein comprising sequences derived from a CS protein of *P. vivax* and the S antigen of Hepatitis B (CSV-S), and
  b. S antigen derived from Hepatitis B virus,
and characterized in that the ratio of S to CSV-S is in the range 0.1 to 1. Suitably, the ratio of S to CSV-S is in the range 0.19 to 0.30 or 0.68 to 0.80.

15 Claims, 24 Drawing Sheets

Figure 1 pBR327
pTDH3
CSV-S
2 micron plasmid
tARG3
pRIT15546
(15550 bp)
LEU2
pBR327

*Plasmid map of pRIT 15607 showing NotI sites, 5'AOX1, CSV-S, 3'AOX1(TT), HIS4, 3'AOX1, and Ampi.*

S/CSV-S ratio: 0.24

SEQUENCE LISTING

<160> NUMBER OF SEQ ID NOS: 11

<210> SEQ ID NO 1
<211> LENGTH: 771
<212> TYPE: DNA
<213> ORGANISM: Artificial Sequence
<220> FEATURE:
<223> OTHER INFORMATION: Pv-CS nucleotide sequence

<400> SEQUENCE: 1
acacattgcg gacataatgt agatttatct aaagctataa atttaaatgg tgtaaacttc      60
aataacgtag acgctagttc actcgggggct gcgcacgtag gtcagtctgc tagcagggggg    120 cgcggtctcg gggaaaaccc agacgacgaa gaaggtgatg ctaaaaagaa aaaggacggt     180
aaaaaagcgg aaccaaaaaa tccaagggaa aataaattaa acagcccggg ggatcgcgcg     240
gatggtcaag cggcgggtaa tggggcgggg ggtcaaccag cggggggatcg cgcggctggt    300 cagccagcgg gggatcgcgc ggctggtcag ccagcggggg atggtgcggc tggccaacca    360 gcggggggatc gcgcggatgg tcagccagcg ggggatcgcg cggatggtca accagccggt    420 gatcgcgcg ctggccaagc ggccggtaat ggggcgggg gtcaagcggc cgcgaacgga      480
gcggggaacc agccaggcgg cggtaacgct gcgaataaaa aagcggaaga tgcgggtgt     540 aacgcgggcg gtaatgcggg cggccaaggt cagaacaacg aagggggctaa tgcaccaaac    600 gaaaaatctg tcaaagaata tctcgataaa gtccgcgcta cagtagggac agaatggacg    660

```
ccatgctctg taacatgtgg tgtcggggta cgcgtgcgcc gccgtgtcaa tgcggctaac    720
aaaaaaccag aagatctcac gttaaatgat ctcgaaacgg atgtctgcac a             771
```

<210> SEQ ID NO 2
<211> LENGTH: 257
<212> TYPE: PRT
<213> ORGANISM: Artificial Sequence
<220> FEATURE:
<223> OTHER INFORMATION: Amino acid sequence of Pv-CS protein

<400> SEQUENCE: 2

```
Thr His Cys Gly His Asn Val Asp Leu Ser Lys Ala Ile Asn Leu Asn
1               5                   10                  15

Gly Val Asn Phe Asn Asn Val Asp Ala Ser Ser Leu Gly Ala Ala His
            20                  25                  30

Val Gly Gln Ser Ala Ser Arg Gly Arg Gly Leu Gly Glu Asn Pro Asp
        35                  40                  45

Asp Glu Glu Gly Asp Ala Lys Lys Lys Asp Gly Lys Lys Ala Glu
    50                  55                  60

Pro Lys Asn Pro Arg Glu Asn Lys Leu Lys Gln Pro Gly Asp Arg Ala
65                  70                  75                  80

Asp Gly Gln Ala Ala Gly Asn Gly Ala Gly Gln Pro Ala Gly Asp
                85                  90                  95

Arg Ala Ala Gly Gln Pro Ala Gly Asp Arg Ala Ala Gly Gln Pro Ala
            100                 105                 110

Gly Asp Gly Ala Ala Gly Gln Pro Ala Gly Asp Arg Ala Asp Gly Gln
        115                 120                 125

Pro Ala Gly Asp Arg Ala Asp Gly Gln Pro Ala Gly Asp Arg Ala Ala
    130                 135                 140

Gly Gln Ala Ala Gly Asn Gly Ala Gly Gly Gln Ala Ala Asn Gly
145                 150                 155                 160

Ala Gly Asn Gln Pro Gly Gly Gly Asn Ala Ala Asn Lys Lys Ala Glu
                165                 170                 175

Asp Ala Gly Gly Asn Ala Gly Gly Asn Ala Gly Gly Gln Gly Gln Asn
            180                 185                 190

Asn Glu Gly Ala Asn Ala Pro Asn Glu Lys Ser Val Lys Glu Tyr Leu
        195                 200                 205

Asp Lys Val Arg Ala Thr Val Gly Thr Glu Trp Thr Pro Cys Ser Val
    210                 215                 220

Thr Cys Gly Val Gly Val Arg Val Arg Arg Val Asn Ala Ala Asn
225                 230                 235                 240

Lys Lys Pro Glu Asp Leu Thr Leu Asn Asp Leu Glu Thr Asp Val Cys
                245                 250                 255

Thr
```

<210> SEQ ID NO 3
<211> LENGTH: 771
<212> TYPE: DNA
<213> ORGANISM: Artificial Sequence
<220> FEATURE:
<223> OTHER INFORMATION: CSV hybrid gene

<400> SEQUENCE: 3

```
acccattgtg gtcacaatgt cgatttgtct aaggccatta acttgaacgg tgttaatttc    60
aacaacgtcg atgcttcttc tttaggtgcc gctcatgttg gtcaatctgc ttcaagaggt   120
```

| | |
|---|---|
| agaggtttag gtgaaaaccc agacgacgaa gaaggtgacg ctaagaagaa gaaggacggt | 180 |
| aagaaggccg aaccaaagaa cccaagagaa acaagttga acaaccagg tgacagagcc | 240 |
| gacggacaag cagctggtaa tggtgctgga ggtcaaccag ctggtgacag agctgccggt | 300 |
| cagcctgctg gtgatagagc tgctggacaa cctgctggag acggtgccgc cggtcaacct | 360 |
| gctggtgata gagcagacgg acaaccagct ggtgaccgtg ctgacggaca gccagccggc | 420 |
| gatagggctg caggtcaagc cgctggtaac ggtgccggtg gtcaagctgc tgctaacggt | 480 |
| gctggtaacc aaccaggtgg tggtaacgct gccaacaaga aagctgaaga cgctggtggt | 540 |
| aatgctggag gtaatgcagg tggtcagggt caaaacaacg aaggtgctaa cgctccaaac | 600 |
| gaaaagtctg ttaaggaata cttagataag gttagagcta ctgtcggtac tgaatggact | 660 |
| ccatgttctg ttacttgtgg tgtcggtgtt agagttagaa gaagagttaa cgccgctaac | 720 |
| aagaagccag aagacttgac tctaaacgac ttggaaactg acgtttgtac t | 771 |

<210> SEQ ID NO 4
<211> LENGTH: 1485
<212> TYPE: DNA
<213> ORGANISM: Artificial Sequence
<220> FEATURE:
<223> OTHER INFORMATION: CSV-S fusion nucleotide sequence

<400> SEQUENCE: 4

| | |
|---|---|
| atgatggctc ccgggaccca ttgtggtcac aatgtcgatt tgtctaaggc cattaacttg | 60 |
| aacggtgtta atttcaacaa cgtcgatgct tcttctttag gtgccgctca tgttggtcaa | 120 |
| tctgcttcaa gaggtagagg tttaggtgaa acccagacg acgaagaagg tgacgctaag | 180 |
| aagaagaagg acgtaagaa ggccgaacca agaacccaa gagaaaacaa gttgaaacaa | 240 |
| ccaggtgaca gagccgacgg acaagcagct ggtaatggtg ctggaggtca accagctggt | 300 |
| gacagagctg ccggtcagcc tgctggtgat agagctgctg gacaacctgc tggagacggt | 360 |
| gccgccggtc aacctgctgg tgatagagca gacggacaac cagctggtga ccgtgctgac | 420 |
| ggacagccag ccggcgatag ggctgcaggt caagccgctg gtaacggtgc cggtggtcaa | 480 |
| gctgctgcta acggtgctgg taaccaacca ggtggtggta acgctgccaa caagaaagct | 540 |
| gaagacgctg gtggtaatgc tggaggtaat gcaggtggtc agggtcaaaa caacgaaggt | 600 |
| gctaacgctc caaacgaaaa gtctgttaag gaatacttag ataaggttag agctactgtc | 660 |
| ggtactgaat ggactccatg ttctgttact tgtggtgtcg gtgttagagt tagaagaaga | 720 |
| gttaacgccg ctaacaagaa gccagaagac ttgactctaa acgacttgga aactgacgtt | 780 |
| tgtactcccg gcctgtgac gaacatggag aacatcacat caggattcct aggacccctg | 840 |
| ctcgtgttac aggcggggtt tttcttgttg acaagaatcc tcacaatacc gcagagtcta | 900 |
| gactcgtggt ggacttctct caattttcta ggggatcac ccgtgtgtct tggccaaaat | 960 |
| tcgcagtccc caacctccaa tcactcacca acctcctgtc ctccaatttg tcctggttat | 1020 |
| cgctggatgt gtctgcggcg ttttatcata ttcctcttca tcctgctgct atgcctcatc | 1080 |
| ttcttattgg ttcttctgga ttatcaaggt atgttgcccg tttgtcctct aattccagga | 1140 |
| tcaacaacaa ccaatacggg accatgcaaa acctgcacga ctcctgctca aggcaactct | 1200 |
| atgtttccct catgttgctg tacaaaacct acggatggaa attgcacctg tattcccatc | 1260 |
| ccatcgtcct gggctttcgc aaaataccta tgggagtggg cctcagtccg tttctcttgg | 1320 |
| ctcagttttac tagtgccatt tgttcagtgg ttcgtagggc tttccccac tgtttggctt | 1380 |
| tcagctatat ggatgatgtg gtattggggg ccaagtctgt acagcatcgt gagtcccttt | 1440 | ataccgctgt taccaattt ctttgtctc tgggtataca tttaa                1485

<210> SEQ ID NO 5
<211> LENGTH: 494
<212> TYPE: PRT
<213> ORGANISM: Artificial Sequence
<220> FEATURE:
<223> OTHER INFORMATION: Amino acid sequence for hybrid fusion protein
      CSV-S

<400> SEQUENCE: 5

```
Met Met Ala Pro Gly Thr His Cys Gly His Asn Val Asp Leu Ser Lys
1               5                   10                  15

Ala Ile Asn Leu Asn Gly Val Asn Phe Asn Asn Val Asp Ala Ser Ser
            20                  25                  30

Leu Gly Ala Ala His Val Gly Gln Ser Ala Ser Arg Gly Arg Gly Leu
        35                  40                  45

Gly Glu Asn Pro Asp Asp Glu Glu Gly Asp Ala Lys Lys Lys Lys Asp
50                  55                  60

Gly Lys Lys Ala Glu Pro Lys Asn Pro Arg Glu Asn Lys Leu Lys Gln
65                  70                  75                  80

Pro Gly Asp Arg Ala Asp Gly Gln Ala Ala Gly Asn Gly Ala Gly Gly
                85                  90                  95

Gln Pro Ala Gly Asp Arg Ala Gly Gln Pro Ala Gly Asp Arg Ala
            100                 105                 110

Ala Gly Gln Pro Ala Gly Asp Gly Ala Ala Gly Gln Pro Ala Gly Asp
        115                 120                 125

Arg Ala Asp Gly Gln Pro Ala Gly Asp Arg Ala Asp Gly Gln Pro Ala
    130                 135                 140

Gly Asp Arg Ala Ala Gly Gln Ala Ala Gly Asn Gly Ala Gly Gly Gln
145                 150                 155                 160

Ala Ala Ala Asn Gly Ala Gly Asn Gln Pro Gly Gly Gly Asn Ala Ala
                165                 170                 175

Asn Lys Lys Ala Glu Asp Ala Gly Gly Asn Ala Gly Gly Asn Ala Gly
            180                 185                 190

Gly Gln Gly Gln Asn Asn Glu Gly Ala Asn Ala Pro Asn Glu Lys Ser
        195                 200                 205

Val Lys Glu Tyr Leu Asp Lys Val Arg Ala Thr Val Gly Thr Glu Trp
    210                 215                 220

Thr Pro Cys Ser Val Thr Cys Gly Val Gly Val Arg Val Arg Arg
225                 230                 235                 240

Val Asn Ala Ala Asn Lys Lys Pro Glu Asp Leu Thr Leu Asn Asp Leu
                245                 250                 255

Glu Thr Asp Val Cys Thr Pro Gly Val Thr Asn Met Glu Asn Ile
            260                 265                 270

Thr Ser Gly Phe Leu Gly Pro Leu Leu Val Leu Gln Ala Gly Phe Phe
        275                 280                 285

Leu Leu Thr Arg Ile Leu Thr Ile Pro Gln Ser Leu Asp Ser Trp Trp
    290                 295                 300

Thr Ser Leu Asn Phe Leu Gly Gly Ser Pro Val Cys Leu Gly Gln Asn
305                 310                 315                 320

Ser Gln Ser Pro Thr Ser Asn His Ser Pro Thr Ser Cys Pro Pro Ile
                325                 330                 335

Cys Pro Gly Tyr Arg Trp Met Cys Leu Arg Arg Phe Ile Ile Phe Leu
            340                 345                 350
```

```
Phe Ile Leu Leu Leu Cys Leu Ile Phe Leu Leu Val Leu Leu Asp Tyr
        355                 360                 365

Gln Gly Met Leu Pro Val Cys Pro Leu Ile Pro Gly Ser Thr Thr Thr
    370                 375                 380

Asn Thr Gly Pro Cys Lys Thr Cys Thr Thr Pro Ala Gln Gly Asn Ser
385                 390                 395                 400

Met Phe Pro Ser Cys Cys Cys Thr Lys Pro Thr Asp Gly Asn Cys Thr
                405                 410                 415

Cys Ile Pro Ile Pro Ser Ser Trp Ala Phe Ala Lys Tyr Leu Trp Glu
                420                 425                 430

Trp Ala Ser Val Arg Phe Ser Trp Leu Ser Leu Leu Val Pro Phe Val
            435                 440                 445

Gln Trp Phe Val Gly Leu Ser Pro Thr Val Trp Leu Ser Ala Ile Trp
    450                 455                 460

Met Met Trp Tyr Trp Gly Pro Ser Leu Tyr Ser Ile Val Ser Pro Phe
465                 470                 475                 480

Ile Pro Leu Leu Pro Ile Phe Phe Cys Leu Trp Val Tyr Ile
                485                 490

<210> SEQ ID NO 6
<211> LENGTH: 3509
<212> TYPE: DNA
<213> ORGANISM: Artificial Sequence
<220> FEATURE:
<223> OTHER INFORMATION: Nucelotide sequence of the RTS expression
      cassette

<400> SEQUENCE: 6
aagcttacca gttctcacac ggaacaccac taatggacac aaattcgaaa tactttgacc      60
ctattttcga ggaccttgtc accttgagcc aagagagcc aagatttaaa ttttcctatg     120
acttgatgca aattcccaaa gctaataaca tgcaagacac gtacggtcaa gaagacatat     180
ttgacctctt aactggttca gacgcgactg cctcatcagt aagacccgtt gaaaagaact     240
tacctgaaaa aaacgaatat atactagcgt tgaatgttag cgtcaacaac aagaagttta     300
atgacgcgga ggccaaggca aaaagattcc ttgattacgt aagggagtta gaatcatttt     360
gaataaaaaa cacgcttttt cagttcgagt ttatcattat caatactgcc atttcaaaga     420
atacgtaaat aattaatagt agtgattttc ctaactttat ttagtcaaaa attagccttt     480
taattctgct gtaacccgta catgcccaaa atagggggcg ggttacacag aatatataac     540
atcgtaggtg tctgggtgaa cagtttatcc ctggcatcca ctaaatataa tggagctcgc     600
ttttaagctg gcatccagaa aaaaaagaa tcccagcacc aaaatattgt tttcttcacc     660
aaccatcagt tcataggtcc attctcttag cgcaactaca gagaacaggg gcacaaacag     720
gcaaaaaacg ggcacaacct caatggagtg atgcaacctg cctggagtaa atgatgacac     780
aaggcaattg acccacgcat gtatctatct cattttctta caccttctat taccttctgc     840
tctctctgat ttggaaaaag ctgaaaaaaa aggttgaaac cagttccctg aaattattcc     900
cctacttgac taataagtat ataaagacgg taggtattga ttgtaattct gtaaatctgt     960
aaatctattt cttaaacttc ttaaattcta cttttatagt tagtcttttt tttagtttta    1020
aaacaccaag aacttagttt cgaataaaca cacataaaca acaaaatga tggctcccga    1080 tcctaatgca aatccaaatg caaacccaaa tgcaaaccca aacgcaaacc ccaatgcaaa    1140
tcctaatgca accccaatg caaatcctaa tgcaaatcct aatgccaatc caaatgcaaa    1200
```

```
tccaaatgca aacccaaacg caaaccccaa tgcaaatcct aatgccaatc caaatgcaaa    1260
tccaaatgca aacccaaatg caaacccaaa tgcaaacccc aatgcaaatc ctaataaaaa    1320
caatcaaggt aatggacaag gtcacaatat gccaaatgac ccaaaccgaa atgtagatga    1380
aaatgctaat gccaacaatg ctgtaaaaaa taataataac gaagaaccaa gtgataagca    1440
catagaacaa tatttaaaga aaataaaaaa ttctatttca actgaatggt ccccatgtag    1500
tgtaacttgt ggaaatggta ttcaagttag aataaagcct ggctctgcta ataaacctaa    1560
agacgaatta gattatgaaa atgatattga aaaaaaaatt tgtaaaatgg aaaagtgctc    1620
gagtgtgttt aatgtcgtaa atagtcgacc tgtgacgaac atggagaaca tcacatcagg    1680
attcctagga cccctgctcg tgttacaggc ggggttttc ttgttgacaa gaatcctcac    1740
aataccgcag agtctagact cgtggtggac ttctctcaat tttctagggg gatcaccgt    1800 gtgtcttggc caaaattcgc agtccccaac ctccaatcac tcaccaacct cctgtcctcc    1860
aatttgtcct ggttatcgct ggatgtgtct gcgcgttta tcatattcct cttcatcctg    1920
ctgctatgcc tcatcttctt attggttctt ctggattatc aaggtatgtt gcccgtttgt    1980
cctctaattc caggatcaac aacaaccaat acgggaccat gcaaaacctg cacgactcct    2040
gctcaaggca actctatgtt tccctcatgt tgctgtacaa aacctacgga tggaaattgc    2100
acctgtattc ccatcccatc gtcctgggct ttcgcaaaat acctatggga gtgggcctca    2160
gtccgtttct cttggctcag tttactagtg ccatttgttc agtggttcgt agggcttcc    2220 cccactgttt ggctttcagc tatatggatg atgtggtatt gggggccaag tctgtacagc    2280
atcgtgagtc cctttatacc gctgttacca attttctttt gtctctgggt atacatttaa    2340
cgaattccaa gctgaaacaa ttcaaaggtt ttcaaatcaa tcaagaactt gtctctgtgg    2400
ctgatccaaa ctacaaattt atgcattgtc tgccaagaca tcaagaagaa gttagtgatg    2460 atgtcttta tggagagcat tccatagtct ttgaagaagc agaaaacaga ttatatgcag    2520
ctatgtctgc cattgatatc tttgttaata ataaaggtaa tttcaaggac ttgaaataat    2580
ccttctttcg tgttcttaat aactaatata taaatacaga tatagatgca tgaataatga    2640
tatacattga ttatttttgca atgtcaatta aaaaaaaaaa atgttagtaa aactatgtta    2700
cattccaagc aaataaagca cttggttaaa cgaaattaac gttttttaaga cagccagacc    2760 gcggtctaaa aatttaaata tacactgcca acaaattcct tcgagttgtc caatttcacc    2820
acttttatat tttcatcaac ttcagcagat tcaaccttct cacatagaac attggaataa    2880
acagccttaa caccactttc aagtttgcac agcgtaatat gaggaatttt gttttgacaa    2940
cacaaccctt taattttctc attgttttca tcaattatgc atccatcttt atctttagac    3000
agttccacta caatagcaat agttttttca tcccaacata gttttttcgag cctaaaattc    3060 agtttgtcgg tcgttttacc tgcgtatttt ggttattacc agagccttgt gcatttcta    3120 tgcggttgtt attgtactcc gttatctggt cagtgtatct gttacaatat gattccacaa    3180
cttttttgcc tcttttcac gggacgacat gacatgacct aatgttatat gaagttcctt    3240
ctgaactttt ccactagcta gtaaatgctt gaatttctca gtcagctctg catcgctagc    3300
aatacacctc ttgaccaatc aataatttca tcgtagtttt ctatttagct gagatatatg    3360
taggtttaat taacttagcg ttttttgttg attattgttg cctttaccaa ctattttct    3420 cacagtaggt ttgtaatcta agctccttct gaacgctgtc tcaatttcat catctttcgg    3480
gatctctggt accaaaattg gataagctt                                      3509
```

```
<210> SEQ ID NO 7
<211> LENGTH: 427
<212> TYPE: PRT
<213> ORGANISM: Artificial Sequence
<220> FEATURE:
<223> OTHER INFORMATION: Predicted translation product of the RTS-HBsAg
      hybrid protein

<400> SEQUENCE: 7
```

| Met | Met | Ala | Pro | As

Val Arg Phe Ser Trp Leu Ser Leu Leu Val Pro Phe Val Gln Trp Phe
        370                 375                 380

Val Gly Leu Ser Pro Thr Val Trp Leu Ser Ala Ile Trp Met Met Trp
385                 390                 395                 400

Tyr Trp Gly Pro Ser Leu Tyr Ser Ile Val Ser Pro Phe Ile Pro Leu
                405                 410                 415

Leu Pro Ile Phe Phe Cys Leu Trp Val Tyr Ile
            420                 425

<210> SEQ ID NO 8
<211> LENGTH: 1485
<212> TYPE: DNA
<213> ORGANISM: Artificial Sequence
<220> FEATURE:
<223> OTHER INFORMATION: Nucleotide sequence CSV-S fusion gene (cloned
      into pHIL-D2 integrative Pichia pastoris expression vector)

<400> SEQUENCE: 8

```
atgatggctc ccgggaccca ttgtggtcac aatgtcgatt tgtctaaggc cattaacttg      60
aacggtgtta atttcaacaa cgtcgatgct tcttctttag gtgccgctca tgttggtcaa     120
tctgcttcaa gaggtagagg tttaggtgaa acccagacg acgaagaagg tgacgctaag      180
aagaagaagg acggtaagaa ggccgaacca agaacccaa gagaaaacaa gttgaaacaa      240
ccaggtgaca gagccgacgg acaagcagct ggtaatggtg ctggaggtca accagctggt     300
gacagagctg ccggtcagcc tgctggtgat agagctgctg acaacctgc tggagacggt      360
gccgccggtc aacctgctgg tgatagagca cgacaac agctggtga ccgtgctgac         420
ggacagccag ccggcgatag ggctgcaggt caagccgctg gtaacggtgc cggtggtcaa     480
gctgctgcta cggtgctgg taaccaacca ggtggtggta cgctgccaa caagaaagct      540
gaagacgctg gtggtaatgc tggaggtaat gcaggtggtc agggtcaaaa caacgaaggt     600
gctaacgctc aaacgaaaa gtctgttaag gaatacttag ataaggttag agctactgtc     660
ggtactgaat ggactccatg ttctgttact tgtggtgtcg gtgttagagt tagaagaaga     720
gttaacgccg ctaacaagaa gccagaagac ttgactctaa cgacttgga aactgacgtt      780
tgtactcccg ggcctgtgac gaacatggag aacatcacat caggattcct aggacccctg    840
ctcgtgttac aggcgggtt tttcttgttg acaagaatcc tcacaatacc gcagagtcta    900
gactcgtggt ggacttctct caattttcta ggggatcac ccgtgtgtct tggccaaaat     960
tcgcagtccc caacctccaa tcactcacca acctcctgtc tccaatttg tcctggttat    1020
cgctggatgt gtctgcggcg ttttatcata ttcctcttca tcctgctgct atgcctcatc   1080
ttcttattgg ttcttctgga ttatcaaggt atgttgcccg tttgtcctct aattccagga   1140
tcaacaacaa ccaatacggg accatgcaaa acctgcacga tcctgctca aggcaactct    1200
atgtttccct catgttgctg tacaaaacct acggatggaa attgcacctg tattcccatc    1260
ccatcgtcct gggctttcgc aaaataccta tgggagtggg cctcagtccg tttctcttgg   1320
ctcagtttac tagtgccatt tgttcagtgg ttcgtagggc tttccccac tgtttggctt    1380
tcagctatat ggatgatgtg gtattggggg ccaagtctgt acagcatcgt gagtcccttt   1440
ataccgctgt taccaatttt cttttgtctc tgggtataca tttaa                   1485
```

<210> SEQ ID NO 9
<211> LENGTH: 494
<212> TYPE: PRT
<213> ORGANISM: Artificial Sequence
<220> FEATURE:

<223> OTHER INFORMATION: Amino-Acid sequence CSV-S fusion protein
      expressed in Pichia pastoris

<400> SEQUENCE: 9

```
Met Met Ala Pro Gly Thr His Cys Gly His Asn Val Asp Leu Ser Lys
1               5                   10                  15

Ala Ile Asn Leu Asn Gly Val Asn Phe Asn Asn Val Asp Ala Ser Ser
            20                  25                  30

Leu Gly Ala Ala His Val Gly Gln Ser Ala Ser Arg Gly Arg Gly Leu
        35                  40                  45

Gly Glu Asn Pro Asp Asp Glu Glu Gly Asp Ala Lys Lys Lys Lys Asp
    50                  55                  60

Gly Lys Lys Ala Glu Pro Lys Asn Pro Arg Glu Asn Lys Leu Lys Gln
65                  70                  75                  80

Pro Gly Asp Arg Ala Asp Gly Gln Ala Ala Gly Asn Gly Ala Gly Gly
                85                  90                  95

Gln Pro Ala Gly Asp Arg Ala Ala Gly Gln Pro Ala Gly Asp Arg Ala
            100                 105                 110

Ala Gly Gln Pro Ala Gly Asp Gly Ala Ala Gly Gln Pro Ala Gly Asp
        115                 120                 125

Arg Ala Asp Gly Gln Pro Ala Gly Asp Arg Ala Asp Gly Gln Pro Ala
    130                 135                 140

Gly Asp Arg Ala Ala Gly Gln Ala Ala Gly Asn Gly Ala Gly Gly Gln
145                 150                 155                 160

Ala Ala Ala Asn Gly Ala Gly Asn Gln Pro Gly Gly Gly Asn Ala Ala
                165                 170                 175

Asn Lys Lys Ala Glu Asp Ala Gly Gly Asn Ala Gly Gly Asn Ala Gly
            180                 185                 190

Gly Gln Gly Gln Asn Asn Glu Gly Ala Asn Ala Pro Asn Glu Lys Ser
        195                 200                 205

Val Lys Glu Tyr Leu Asp Lys Val Arg Ala Thr Val Gly Thr Glu Trp
    210                 215                 220

Thr Pro Cys Ser Val Thr Cys Gly Val Gly Val Arg Val Arg Arg Arg
225                 230                 235                 240

Val Asn Ala Ala Asn Lys Lys Pro Glu Asp Leu Thr Leu Asn Asp Leu
                245                 250                 255

Glu Thr Asp Val Cys Thr Pro Gly Pro Val Thr Asn Met Glu Asn Ile
            260                 265                 270

Thr Ser Gly Phe Leu Gly Pro Leu Leu Val Leu Gln Ala Gly Phe Phe
        275                 280                 285

Leu Leu Thr Arg Ile Leu Thr Ile Pro Gln Ser Leu Asp Ser Trp Trp
    290                 295                 300

Thr Ser Leu Asn Phe Leu Gly Gly Ser Pro Val Cys Leu Gly Gln Asn
305                 310                 315                 320

Ser Gln Ser Pro Thr Ser Asn His Ser Pro Thr Ser Cys Pro Pro Ile
                325                 330                 335

Cys Pro Gly Tyr Arg Trp Met Cys Leu Arg Arg Phe Ile Ile Phe Leu
            340                 345                 350

Phe Ile Leu Leu Leu Cys Leu Ile Phe Leu Leu Val Leu Leu Asp Tyr
        355                 360                 365

Gln Gly Met Leu Pro Val Cys Pro Leu Ile Pro Gly Ser Thr Thr Thr
    370                 375                 380

Asn Thr Gly Pro Cys Lys Thr Cys Thr Thr Pro Ala Gln Gly Asn Ser
385                 390                 395                 400
```

```
Met Phe Pro Ser Cys Cys Cys Thr Lys Pro Thr Asp Gly Asn Cys Thr
                405                 410                 415

Cys Ile Pro Ile Pro Ser Ser Trp Ala Phe Ala Lys Tyr Leu Trp Glu
            420                 425                 430

Trp Ala Ser Val Arg Phe Ser Trp Leu Ser Leu Leu Val Pro Phe Val
        435                 440                 445

Gln Trp Phe Val Gly Leu Ser Pro Thr Val Trp Leu Ser Ala Ile Trp
    450                 455                 460

Met Met Trp Tyr Trp Gly Pro Ser Leu Tyr Ser Ile Val Ser Pro Phe
465                 470                 475                 480

Ile Pro Leu Leu Pro Ile Phe Phe Cys Leu Trp Val Tyr Ile
                485                 490

<210> SEQ ID NO 10
<211> LENGTH: 681
<212> TYPE: DNA
<213> ORGANISM: Artificial Sequence
<220> FEATURE:
<223> OTHER INFORMATION: Nucleotide sequence S gene (cloned into pPICZ-A
      integrative Pichia pastoris vector)

<400> SEQUENCE: 10
atggagaaca tcacatcagg attcctagga cccctgctcg tgttacaggc ggggtttttc      60
ttgttgacaa gaatcctcac aataccgcag agtctagact cgtggtggac ttctctcaat     120
tttctagggg gatcacccgt gtgtcttggc caaaattcgc agtccccaac ctccaatcac     180
tcaccaacct cctgtcctcc aatttgtcct ggttatcgct ggatgtgtct gcggcgtttt     240
atcatattcc tcttcatcct gctgctatgc ctcatcttct tattggttct tctggattat     300
caaggtatgt tgcccgtttg tcctctaatt ccaggatcaa caacaaccaa tacgggacca     360
tgcaaaacct gcacgactcc tgctcaaggc aactctatgt ttccctcatg ttgctgtaca     420
aaacctacgg atggaaattg cacctgtatt cccatcccat cgtcctgggc tttcgcaaaa     480
tacctatggg agtgggcctc agtccgtttc tcttggctca gtttactagt gccatttgtt     540
cagtggttcg tagggctttc ccccactgtt tggctttcag ctatatggat gatgtggtat     600
tgggggccaa gtctgtacag catcgtgagt ccctttatac cgctgttacc aattttcttt     660
tgtctctggg tatacattta a                                               681

<210> SEQ ID NO 11
<211> LENGTH: 226
<212> TYPE: PRT
<213> ORGANISM: Artificial Sequence
<220> FEATURE:
<223> OTHER INFORMATION: Amino Acid sequence S protein

<400> SEQUENCE: 11

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Ser Pro Val Cys
        35                  40                  45

Leu Gly Gln Asn Ser Gln Ser Pro Thr Ser Asn His Ser Pro Thr Ser
    50                  55                  60

Cys Pro Pro Ile Cys Pro Gly Tyr Arg Trp Met Cys Leu Arg Arg Phe
65                  70                  75                  80
```

-continued

```
Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Thr Thr Thr Asn Thr Gly Pro Cys Lys Thr Cys Thr Thr Pro Ala
            115                 120                 125

Gln Gly Asn Ser Met Phe Pro Ser Cys Cys Cys Thr Lys Pro Thr Asp
        130                 135                 140

Gly Asn Cys Thr Cys Ile Pro Ile Pro Ser Ser Trp Ala Phe Ala Lys
145                 150                 155                 160

Tyr Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Ala Ile Trp Met Met Trp Tyr Trp Gly Pro Ser Leu Tyr Ser Ile
            195                 200                 205

Val Ser Pro Phe Ile Pro Leu Leu Pro Ile Phe Phe Cys Leu Trp Val
        210                 215                 220

Tyr Ile
225
```

VACCINES FOR MALARIA

This application is the US National Stage of International Application No. PCT/EP2008/068130, filed 22 Dec. 2008, which claims benefit of the filing dates of US Provisional Applications No. 61/016,522, filed 24 Dec. 2007, and No. 61/016,525, filed 24 Dec. 2007, which are incorporated herein by reference in its entirety.

The present invention relates to a novel lipoprotein particle, methods for preparing and purifying the same, its use in medicine, particularly in the prevention of malarial infections, compositions/vaccines containing the particles or antibodies against the protein particle such as monoclonal or polyclonal antibodies and use of the same, particularly in therapy.

Malaria, is one of the world's major health problems with more than 2 to 4 million people dying from the disease each year. One of the most prevalent forms of the disease is caused by the protozoan parasite *P. vivax*, which is found in tropical and sub-tropical regions. Interestingly the parasite can complete its mosquito cycle at temperatures as low as 15 degrees Celsius, which has allowed the disease to spread in temperate climates.

One of the most acute forms of the disease is caused by the protozoan parasite, *Plasmodium falciparum* (*P. falciparum*) which is responsible for most of the mortality attributable to malaria.

The life cycle of *Plasmodium* is complex, requiring two hosts, man and mosquito for completion. The infection of man is initiated by the inoculation of sporozoites into the blood stream through the bite of an infected mosquito. The sporozoites migrate to the liver and there infect hepatocytes where they differentiate, via the exoerythrocytic intracellular stage, into the merozoite stage which infects red blood cells (RBC) to initiate cyclical replication in the asexual blood stage. The cycle is completed by the differentiation of a number of merozoites in the RBC into sexual stage gametocytes, which are ingested by the mosquito, where they develop through a series of stages in the midgut to produce sporozoites which migrate to the salivary gland.

Due to the fact that the disease caused by *P. vivax* is rarely lethal, efforts to prevent and treat malaria have been focused on the more deadly form of the disease caused by *Plasmodium falciparum* (*P. falciparum*).

Although the disease caused by *P. vivax* does not usually result in death of the patient, due to the volume of cases, which seems to be increasing, the significant impact on the quality of life of the patient, the increasing reports of the severe incidences of the disease resulting in anemia and death, and the economic impact, an effective vaccination for the disease is still required. Furthermore, a single vaccine able to provide protection against both causes of the disease would be advantageous.

A feature of the *P. vivax* is that some strains are capable of causing delayed infection by remaining latent in the liver before emerging into the peripheral circulation to manifest clinical symptoms. Thus individuals, for example when traveling through an infected area, may be infected and yet may not exhibit symptoms for several months. This has the potential to cause the spread of the disease and for this reason persons traveling to infected areas are not allowed to donate blood for transfusion for a defined period of time after traveling to the infected region.

*P. vivax* malaria infection remains latent within the liver while the parasite is undergoing pre-erthrocytic shizogony. If the parasite is controlled at this stage, before it escapes the liver, no clinical symptoms of the disease, are observed in the patient.

The sporozoite stage of *Plasmodium* has been identified as a potential target of a malaria vaccine. Vaccination with deactivated (irradiated) sporozoite has been shown to induced protection against experimental human malaria (Am. J, Trop. Med. Hyg 24: 297-402, 1975). However, it is has not been possible practically and logistically to manufacture a vaccine for malaria for the general population based on this methodology, employing irradiated sporozoites.

The major surface protein of the sporozoite is known as circumsporozoite protein (CS protein). It is thought to be involved in the motility and invasion of the sporozoite during its passage from the initial site of inoculation by the mosquito into the circulation, where it migrates to the liver.

The CS protein of *Plasmodia* species is characterized by a central repetitive domain (repeat region) flanked by non-repetitive amino (N-terminus) and carboxy (C-terminus) fragments. The central domain of *P. vivax* is composed of several blocks of a repeat unit, generally of nine tandem amino acids.

In certain Asian strains, after the central repeat region, an additional sequence of approximately 12 amino acids is present. The function of the latter is not known. However, it is hypothesized, by some, that said amino acids may be linked to the delayed onset of clinical symptoms of the disease, although this has not been investigated. It is thought that the N-terminus is characterised by a sequence of 5 amino acids known as region I. It is also thought that the C-terminus is characterised by comprising a sequence of 12 amino acids known as region II. The latter contains a cell-adhesive motif, which is highly conserved among all malaria CS protein.

WO 93/10152 and WO 98/05355 describe a vaccine derived from the CS protein of *P. falciparum* and it seems that there has been some progress made towards the vaccination against *P. falciparum* using the approach described therein, see also Heppner et al. 2005, Vaccine 23, 2243-50.

The CS protein in *P. falciparum* has a central repeat region that is conserved. In contrast at least two forms (designated VK210 or type I and VK247 or type II) of the CS protein for *P. vivax* are known. This renders it more difficult to identify a construct of the CS protein with all the desired properties such as immogenicity, which provides general protection against *P. vivax* regardless of the specific type of CS protein because antibodies directed the central repeating region of type I do not necessarily recognize epitopes on the corresponding region of type II and vice versa.

A recombinant *P. vivax* CS protein was expressed and tested as a vaccine in the 1980-1990's with limited success (Collins et al., 1989. Am. J. Trop. Med. Hyg. 40, 455-64). Some work has been done to develop a vaccine based on Multiple Antigen Peptides (MAP) employing one or more epitopes that are cross-linked (Nardelli and Tam, 1995, Pharm. Biotechnol. 6, 803-19).

The present invention provides an antigenic particle for use in malaria vaccines, which is believed to produce at least a humoral response and possibly also a cellular immune response. The antigen may also induce T helper cells, for example Th1 and/or Th2 cells.

Accordingly, the present invention provides an immunogenic protein particle comprising the following monomers:
  a. a fusion protein comprising sequences derived from a CS protein of *P. vivax* and the S antigen of Hepatitis B (CSV-S), and b. S antigen derived from Hepatitis B virus,
and characterised in that the ratio of S to CSV-S is in the range 0.1 to 1.

Suitably, the ratio of S to CSV-S is in the range 0.19 to 0.30, for example 0.2 to 0.25 such as about or substantially 0.24, or in the range 0.68 to 0.80 such as about or substantially 0.73.

The S antigen in part b) will generally be unfused S antigen.

Sequence Listing

SEQ. ID. No. 1 Nucleotide sequence of the hybrid protein CSV (optimized for expression in *E. Coli*)

SEQ. ID. No. 2 Amino acid sequence of the hybrid protein CSV

SEQ. ID. No. 3 Nucleotide sequence for the hybrid protein CSV (optimized for expression in yeast)

SEQ. ID. No. 4 Nucleotide sequence for the hybrid fusion protein CSV-S

SEQ. ID. No. 5 Amino acid sequence for the hybrid fusion protein CSV-S

SEQ. ID No. 6&7 Nucleotide Sequence for an RTS expression cassette and predicted RTS protein.

SEQ ID. No. 8 Nucleotide sequence CSV-S fusion gene (cloned into pHIL-D2 integrative *Pichia pastoris* expression vector)

SEQ ID. No. 9 Amino acid sequence of CSV-S fusion protein expressed in *Pichia pastoris*

SEQ ID. No. 10 Nucleotide sequence of S gene (cloned into pPICZ-A integrative *Pichia pastoris* vector)

SEQ ID. No. 11 Amino acid sequence encoded by Seq ID No 10

FIGURES

FIG. 1 Plasmid map for pRIT15546 is a yeast episomal vector.

FIG. 2 Plasmid map of pGF1-S2a plasmid prepared by GSK employed in "fusing" the desired antigen with the S antigen from Hepatitis B. Cloning heterologous DNA sequences between SmaI sites (after excision of the 12 bp SmaI DNA fragment) creates in-frame fusion with the S gene.

FIG. 3 Plasmid map of pRIT15582
Digestion with XhoI liberates a 8.5 kb linear DNA fragment carrying the CSV-S expression cassette plus the LEU2 selective marker, being used for insertion into the yeast chromosome.

FIG. 4 Restriction map of the linear XhoI fragment used to integrate CSV-S cassette FIG. 5 Western blot of recombinant proteins expressed in strain Y1835.
Panel A: WB revealed with anti-S antibody
Samples loaded (100 µg total protein/well):
1: Y1631 (RTS,S producing strain, as comparison)
2: Y1835
3: Y1835
4: Y1834
Panel B: WB revealed with anti-CSV antibody
Samples loaded (100 µg total protein/well):
1: Y1631 (RTS,S producing strain, as comparison)
2: Y1295
3: Y1835
4: Y1834
5: nr (another construct CSVS)
6: nr (another construct —S antigen only)

FIG. 6 Electron micrograph of CSV-S,S mixed particles produced in strain Y1835
CSV-S,S particles were purified from soluble cell extracts (based on RTS,S purification process) and submitted to electron microscopy analysis. Particles were visualized after negative staining with phosphotungstic acid. The scale is equivalent to 100 nm.

Figure 7:
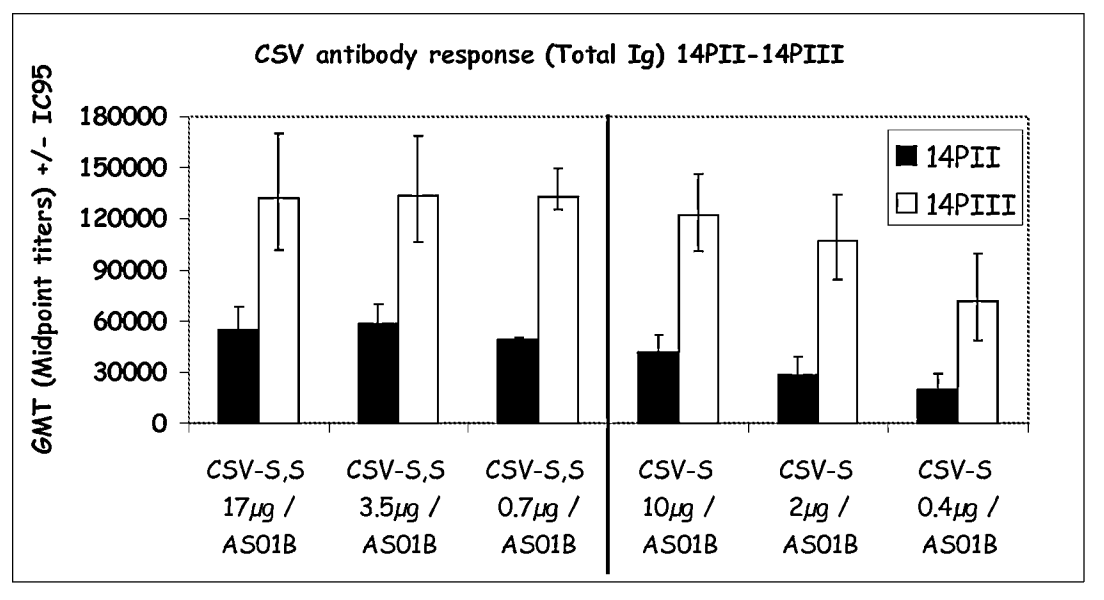

FIG. 7 CSV-specific Ab response (Anti-CSV serology (Ig total))

FIG. 8 HBs-specific Ab response

FIG. 9 CSV-specific Ab response (14pII)
(ELISA Mouse Ig Total Anti-Csv 14pII)

Figure 10:
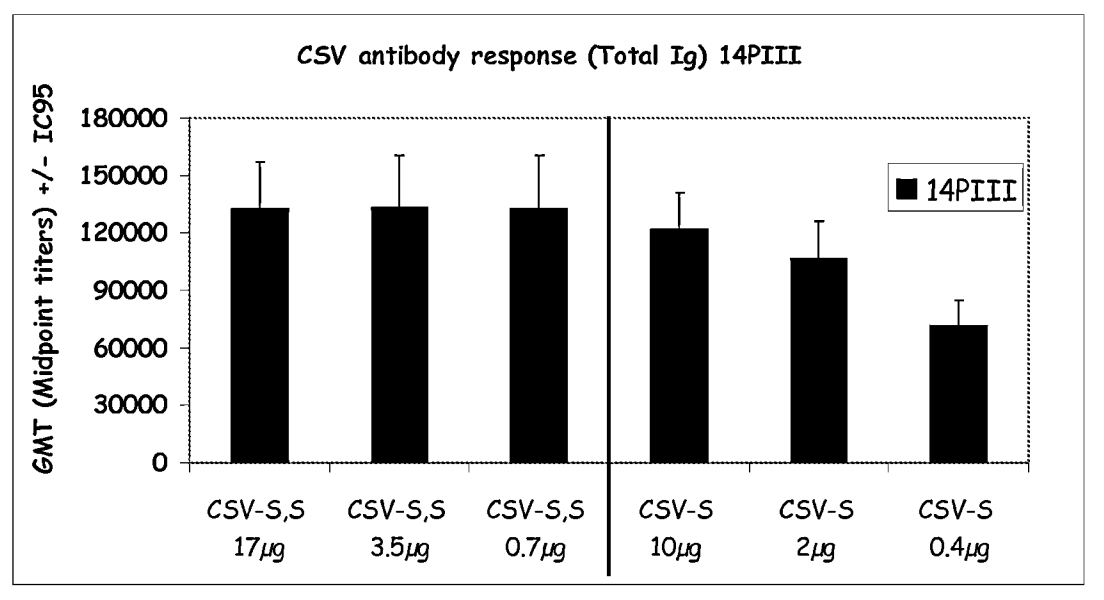

FIG. 10 CSV-specific Ab response (14pIII)
(ELISA Mouse Ig Total Anti-Csv 14pIII)

FIG. 11 HBs-specific Ab response (14pII)

FIG. 12 HBs-specific Ab response (14pIII)

FIG. 13 CSV-specific Ab response (14pII)
(ELISA Mouse Ig Total Anti-Csv 14pII)

FIG. 14 CSV-specific Ab response (14pIII)
(ELISA Mouse Ig Total Anti-Csv 14pIII)

FIG. 15 HBs-specific Ab response (14pII)

FIG. 16 HBs-specific Ab response (14pIII)

FIG. 17 Shows a gel employed to calculate the ratio of S:CVS-S. S/CSVS ratio: 0.73 (Y1835 CSV-S,S purified particles: determination of S/CSV-S ratio)

FIG. 18 Plasmid map for pRIT15607 containing CSV-S gene.

Figure 19:
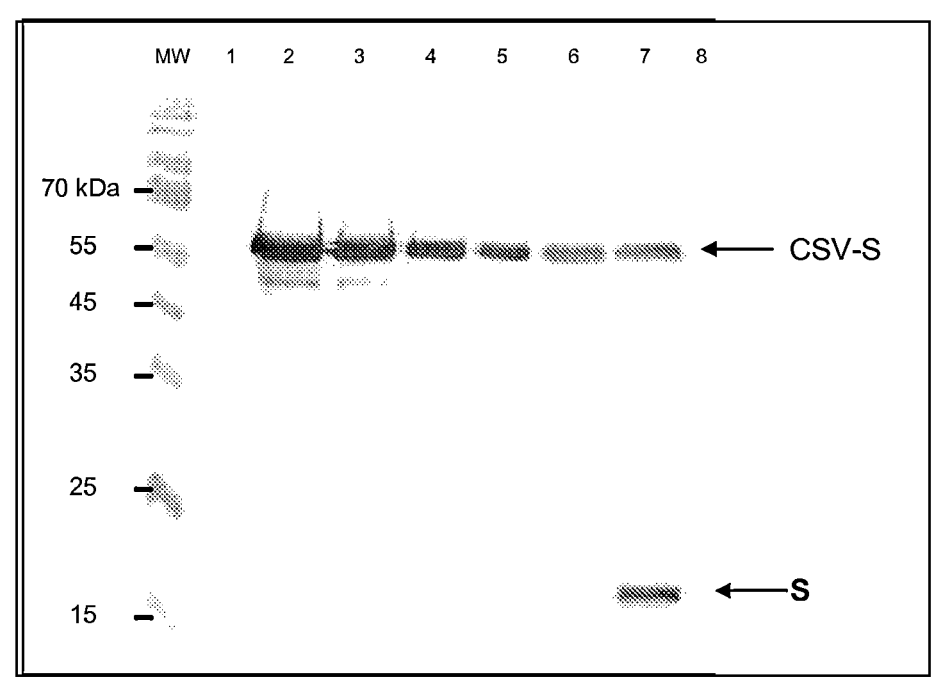

FIG. 19 A Western Blot of recombinant protein expressed in strain Y1840.
WB revealed with anti-S antibody. Quantity of total protein loaded is in brackets:
1: GS115 (*Pichia pastoris* host cell)
2: Y1840 (100 µg)
3: Y1840 (50 µg)
4: Y1840 (25 µg)
5: Y1840 (12.5 µg)
6: Y1833 (100 µg, S.c. strain expressing CSV-S)
7: Y1835 (100 µg, S.c. strain co-expressing CSV-S and S)

FIG. 20 Plasmid map for pRIT15607

FIG. 21 A Western Blot of recombinant proteins expressed in strain Y1847.
WB revealed with anti-S antibody. Samples loaded (20 µg total protein per well):
1: Y1835
2: Y1840
3: Y1847

Figure 22:
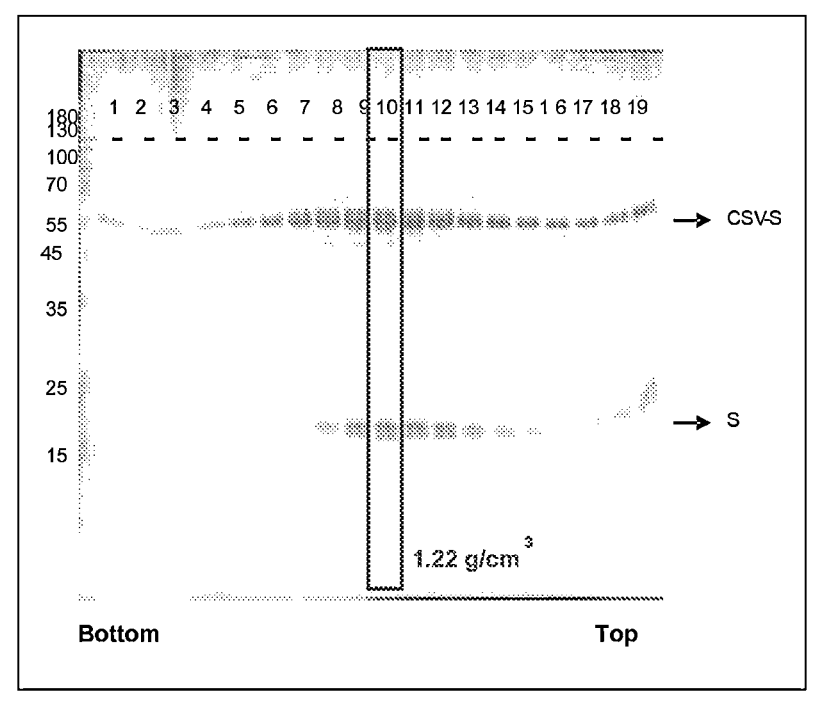

FIG. 22 A cesium chloride gradient of the cell-free extract prepared from strain Y1847

FIG. 23 Electron micrograph of CSV-S,S particles produced in strain Y1847 purified from soluble cell extracts & submitted to electron microscopy analysis. Particles were visualized after negative staining with phosphotungstic acid. The scale is equivalent to 100 nm.

FIG. 24 Y1847 CSV-S,S purified particles for determination of the S to CSV-S ratio. S/CSVS ratio: 0.24.

In the figures where the response measured is CSV specific then the response to the CSV element in each entity is being measured, be it fusion protein CSV-S or particles CSV-S,S.

In one embodiment of the invention there are thought to be about 7.5 S antigen molecules for each molecule of CSV-S, for example based on the relative density of each component.

Surprisingly, the particles of the invention seem to be more immunogenic at least in some aspects, when tested in vivo in mice than corresponding so-called simple particles. The latter are virus like particle made up primarily of the fusion protein component CSV-S and which do NOT contain any unfused S antigen. Whilst not wishing to be bound by theory it is thought that in mixed particles, comprising CSV-S and unfused S antigen according to the invention, the CSV-S components are arranged or orientated in a favourable way, which optimizes the immune response thereto.

A further advantage of the particles according to the invention is that there is a potential to use these particles at a lower dose whilst eliciting the same or similar level of immune response as simple CSV-S particles, which do not contain unfused S antigen.

In certain hosts, such as yeast cells, once expressed the fusion protein (comprising the S antigen) is spontaneously assembled into a protein structure/particle composed of numerous monomers of said fusion proteins. When the chosen recipient yeast strain already carries in its genome one or more integrated copies of Hepatitis B S expression cassettes then the particles assembled may also include monomers of unfused S antigen.

Furthermore particle with the specific ratio can be prepared by employing yeast, *Saccharomyces cerevisiae* such as DC5 in ATCC data base (accession number 20820), under the name RIT DC5 cir(o). Depositor: Smith Kline-RIT). Advantageously such yeast are suitable for commercial production of the particles according to the invention.

Furthermore particles with the specific ratio herein can be prepared by employing yeast, *Pichia pastoris*. Advantageously such yeast are suitable for commercial production of the particles according to the invention. Furthermore, a high yield of particles is obtained, particularly when the certain promoters are employed. The yields for pastoris are higher than those where the corresponding DNA is expressed in *Saccharomyces cerevisiae*. In some instances the yields may be 10 times or more those obtained when *Saccharomyces cerevisiae* is employed.

The yeast may contain 1, 2, 3, 4, or 5 such as 4 copies of CSV-S in its genome.

In one aspect the yeast is recombinant yeast strain Y1835.

In one aspect the yeast is recombinant yeast strain Y1847.

The ratio referred to herein is an average, for example based on a calculation of the density of the S antigen band and the CSV-S band in an appropriate gel (see for example FIGS. 17 and 24).

Various approaches can be used to engineer yeast for the preparation of said particles, for example an expression cassette for the fusion protein can be inserted into the genome of a yeast already containing at least one expression cassette for S antigen. A skilled person working in the field is well able to prepare a suitable host for the preparation of particles according to the invention. Further details are provided below.

Whilst not wishing to be bound by theory it is thought that the surfactants, for example Tween such as Tween 20 or 80 used to liberate the particle from the yeast cells may assist in the stabilization of the lipoprotein particles.

CSV-S

The fusion protein CSV-S employed in the invention comprises: a portion derived from the CS protein of *P. vivax* (CSV). This CSV antigen may be a native protein such as found in type I CS proteins of *P. vivax* and/or as found in type II proteins of *P. vivax*. Alternatively the CSV protein may be a hybrid protein or chimeric protein comprising elements from said type I and II CS proteins. When the latter is fused to S antigen this will be referred to herein as a hybrid fusion protein.

CSV-S is used herein as a generic term to cover fusion proteins comprising a sequence/fragment form the CS protein of *P. vivax* and a sequence/fragment from the S-antigen of Hepatitis B.

*P. vivax* with type I CS proteins is more prevalent than *P. vivax* with type II CS proteins. Therefore in one aspect the invention employs a CS protein from type I. In an alternative aspect the invention provides a hybrid protein comprising a repeat unit from type I and a repeat unit from type II, for example wherein more repeat units from type I are included in the hybrid than repeat units of type II.

The hybrid/chimeric protein will generally comprise:
at least one repeat unit derived from the central repeat section of a type I
circumsporozoite protein of *P. vivax*, and
at least one repeat unit derived from the central repeating section of a type II
circumsporozoite protein of *P. vivax*.

Any suitable strain of *P. vivax* may be employed in the invention including: Latina, America (ie Sal 1, Belem), Korean, China, Thailand, Indonesia, India, and Vietnam. The construct in SEQ ID No 2 is based on a Korean strain (more specifically a South Korean strain).

It is believed that the presence of the surface antigen from Hepatitis B boosts the immunogenicity of the CS protein portion, aids stability, and/or assists reproducible manufacturing of the protein.

In an embodiment the hybrid fusion protein (CSV-S) has the amino acid sequence shown in SEQ ID No. 5. In the sequence amino acids 6 to 262 are derived from CSV and 269 to 494 are derived from S. The remaining amino acids are introduced by genetic construction (which, in particular may be varied as appropriate). The four amino acids, Met, Met Ala Pro, are derived specifically from plasmid pGF1-S2 (see FIG. 4)

The nucleotide sequence for protein of SEQ ID No 5 is given in SEQ ID No 4.

In one embodiment the particle according to the invention is provided in a liquid formulation comprising an antioxidant, for example an antioxidant containing an thiol functional group, for example monothioglycerol, N-acetyl cysteine, cysteine, glutathione or mixtures thereof. The liquid formulation may be provided as one or two doses for reconstitution with an appropriate adjuvant. The formulation may be provided in, for example a glass vial such as 3 mL glass vial as appropriate. In one aspect the vial is amber. In an alternative or additional aspect oxygen is excluded from the formulation.

In one embodiment the particle according to the invention may be provided in a lyophilized form, optionally in association/combination with a suitable antioxidant for example an antioxidant containing an thiol functional group, such as monothioglycerol, N-acetyl cysteine, cysteine, glutathione or mixtures thereof.

In an alternative aspect the hybrid fusion proteins of the invention comprise a portion derived from a mutant S protein, for example as described in published US application No. 2006/194196 (also published as WO 2004/113369). This document describes a mutant labeled HDB05. In particular it describes comparisons of the mutant and wild type proteins in FIGS. 1 and 6 and genes for the mutant in FIGS. 4 and 5. Sequences 12 to 22 therein describe particular polypeptides of the mutant S protein. Each of the above is incorporated herein by reference.

The fusion protein CSV-S may for example be prepared employing the plasmid pGF1-S2 (see FIG. 2 and the examples for further details), which when the appropriate sequence corresponding to CSV is inserted at the SmaI cloning site can under suitable conditions produce the fusion protein CSV-S.

The vector pRIT15546 is a yeast episomal expression vector (2μ-based vector) carrying the CSV-S expression cassette. The recombinant expression is driven by a promoter derived from the yeast TDH3 gene (constitutive expression). The construction of pRIT15546 vector is detailed below.

Construction of pRIT15546 vector.

A CSV synthetic gene, with an appropriate codon usage for yeast expression was constructed and sub-cloned into pUC57 vector (GenBank/EMBL accession number Y14837). The resulting plasmid pUC57/CSV and the yeast expression vector pGf1-S2 were both restricted with the appropriate enzyme. The vector pGf1-S2 was constructed (at GSK) by a multistep cloning procedure. This vector, which already carries an S expression cassette, allows the construction of fusion genes, as N-terminal in-frame fusion with the S gene of Hepatitis B virus. The final expression vector, after sequence verification, was named pRIT15546 (FIG. 8).

The DNA sequences encoding the proteins of the present invention are, in one embodiment flanked by transcriptional control elements, for example derived from yeast genes and incorporated into an expression vector.

*Saccharomyces cerevisiae*

An expression cassette for hybrid proteins of the invention may, for example, be constructed comprising the following features:

A promoter sequence, derived, for example, from the *S. cerevisiae* TDH3 gene.

A sequences encoding for an appropriate fusion protein.

A transcription termination sequence contained within the sequence, derived, for example, from the *S. cerevisiae* ARG3 gene.

An example of a suitable promoter is the promoter from the *S. cerevisiae* TDH3 gene Musti et al.

A suitable plasmid can then be employed to insert the sequence encoding for the hybrid fusion protein into a suitable host for synthesis. An example of a suitable plasmid is pRIT15546 a 2 micron-based vector for carrying a suitable expression cassette, see FIG. 1 and Examples for further details.

The plasmid will generally contain an in-built marker to assist selection, for example a gene encoding for antibiotic resistance or LEU2 or HIS auxotrophy.

As discussed above use of *Saccharomyces cerevisiae* with a cassette encoding CSV-S and at least one cassette encoding for S antigen from Hepatitis B may be employed to provide particles according to the invention.

Generally the host will have an expression cassette for each fusion protein in the particle and will also have one or more expression cassettes for the S antigen integrated in its genome.

In one embodiment the yeast has 1, 2, 3, 4, 5 or 6 such as 4 or 5 copies of S antigen integrated.

Thus the invention also extends to a host comprising a polynucleotide such as DNA encoding for two or more components of a particle according to the present invention.

The invention extends to a *Saccharomyces cerevisiae* comprising a cassette encoding for CSV-S and at least one cassette encoding S antigen.

The nucleotide sequences or part thereof (such as the portion encoding the CS/hybrid protein but optionally not the portion encoding protein S) employed herein may be codon-optimized for expression in a host, such as yeast.

The invention also extends to use of *Saccharomyces cerevisiae* particularly Y1835 to prepare particles according to the invention.

A further aspect of the present invention provides a process for the preparation of particles of the invention, which process comprises expressing DNA sequence encoding the protein, in *Saccharomyces cerevisiae*, for example recombinant yeast Y1835, and optionally the further step of recovering the product.

The invention also extends to products obtainable from the process of expressing DNA encoding CSV-S, particularly a hybrid fusion protein as described herein, and DNA encoding S antigen from Hepatitis B in a yeast such as *Saccharomyces cerevisiae*.

*Pichia pastoris*

An expression cassette for hybrid proteins of the invention may, for example, be constructed comprising the following features:

A promoter sequence, derived, for example, from the *P. pastoris* AOX1 gene.

A sequences encoding for an appropriate fusion protein.

A transcription termination sequence contained within the sequence, derived, for example, from the *P. pastoris* AOX1 gene regulatory elements.

An example of a suitable promoter is the promoter from the *P. pastoris* AOX1 gene. The AOX promoter is a very strong and tightly regulated promoter that usually provides high yields of recombinant protein. Generally 10 fold higher yields than yields in *Saccharomyces cerevisiae* are obtained when this promoter is employed to prepare particles of the invention.

An alternative promoter that may be employed with *P. pastoris* is a GAP promoter.

A suitable plasmid can then be employed to insert the sequence encoding for the hybrid fusion protein into a suitable host for synthesis. An example of a suitable plasmid is pRIT15546 a 2 micron-based vector for carrying a suitable expression cassette.

The plasmid will generally contain an in-built marker to assist selection, for example a gene encoding for antibiotic resistance or LEU2 or HIS auxotrophy.

As discussed above use of *Pichia pastoris* with a cassette encoding CSV-S and at least one cassette encoding for S antigen from Hepatitis B may be employed to provide particles according to the invention.

Generally the host will have an expression cassette for each fusion protein in the particle and will also have one or more expression cassettes for the S antigen integrated in its genome.

In one embodiment the yeast has 1, 2, 3, 4, 5 or 6, such 4 or 5 copies of S antigen integrated.

The invention also extends to a host comprising a polynucleotide such as DNA encoding for two or more components of a particle according to the present invention.

The invention extends to a *Pichia pastoris* comprising a cassette encoding for CSV-S and at least one cassette encoding S antigen.

The nucleotide sequences or part thereof (such as the portion encoding the CS/hybrid protein but optionally not the portion encoding protein S) employed herein may be codon-optimized for expression in a host, such as yeast.

The invention also extends to use of *Pichia pastoris* particularly Y1847 to prepare particles according to the invention.

A further aspect of the present invention is to provide a process for the preparation of particles of the invention, which process comprises expressing DNA sequence encoding the protein, in *Pichia pastoris*, for example recombinant yeast Y1847, and recovering the product.

The invention also extends to processes of purifying the particles according to the invention comprising precipitation steps, ion exchange and gel permeation chromatography, and caesium chloride ultracentrifugation.

The present invention also relates to composition or vaccines comprising a protein particle according to the invention for use in combination with a further active ingredient, particularly for the treatment or prevention of malaria, such as in admixture with the same.

The present invention also relates to compositions or components for use in a vaccine which comprise the particles herein and also to vaccines comprising a protein particle according to the invention in admixture with a suitable excipient.

Component for a vaccine as used herein relates to an entity comprising the particles of the invention and at least one excipient and suitable for inclusion into a vaccine. A component for a vaccine will generally not include adjuvant components.

Vaccine in the context of the present specification relates to a formulation comprising a particle and stabilizing agent, excipients and all adjuvant components, wherein the formulation is suitable for injection into a human.

Formulations

In the context of this specification excipient, refers to a component in a pharmaceutical formulation with no therapeutic effect in its own right. A diluent or liquid carrier falls within the definition of an excipient. An adjuvant also falls within the definition of an excipient because whilst adjuvants are capable of stimulating an immune response, in the absence of a therapeutic component the immune response is non-specific.

Immunogenic in the context of this specification is intended to refer to the ability to elicit a specific immune response to the malaria component or S antigen component. This response may, for example be when the lipoprotein particle is administered at an appropriate dose and in an appropriate formulation which may include/require a suitable adjuvant. A booster comprising a dose similar or less than the original dose may be required to obtain the required immunogenic response.

The composition/pharmaceutical formulations according to the invention may also include in admixture one or more further antigens such as those derived from *P. falciparium* and/or *P. vivax*, for example wherein the antigen is selected from DBP such as Pv RII the receptor binding domain of DBP, PvTRAP, PvMSP2, PvMSP4, PvMSP5, PvMSP6, PvMSP7, PvMSP8, PvMSP9, PvAMA1 and RBP or fragment thereof.

Other example, antigens derived from *P. falciparum* include, PfEMP-1, Pfs 16 antigen, MSP-1, MSP-3, LSA-1, LSA-3, AMA-1 and TRAP. Other *Plasmodium* antigens include *P. falciparum* EBA, GLURP, RAPT, RAP2, Sequestrin, Pf332, STARP, SALSA, PfEXP1, Pfs25, Pfs28, PFS27/25, Pfs48/45, Pfs230 and their analogues in other *Plasmodium* spp.

The compositions/pharmaceutical formulations according to the invention may also comprise particles of RTS, S (as described in WO 93/10152) in admixture with the particles according to the invention.

In a vaccine of the invention, an aqueous solution of the particle may be used directly. Alternatively, the particle with or without prior lyophilisation can be mixed or absorbed with any of the known adjuvants.

Adjuvants

In an embodiment the adjuvant is a Toll like receptor (TLR) 4 ligand, for example an agonist such as a lipid A derivative particularly monophosphoryl lipid A or more particularly 3-deacylated monophoshoryl lipid A (3D-MPL).

3-Deacylated monophosphoryl lipid A is known from U.S. Pat. No. 4,912,094 and UK patent application No. 2,220,211 (Ribi) and is available from Ribi Immunochem, Montana, USA and old under the trademark MPL® by Corixa corporation. 3D-MPL primarily promotes CD4+ T cell responses with an IFN-g (Th1) phenotype. It can be produced according to the methods disclosed in GB 2 220 211 A. Chemically it is a mixture of 3-deacylated monophosphoryl lipid A with 3, 4, 5 or 6 acylated chains. Suitably in the compositions of the present invention small particle 3D-MPL may be used. Small particle 3D-MPL has a particle size such that it may be sterile-filtered through a 0.22 nm filter. Such preparations are described in WO 94/21292. Synthetic derivatives of lipid A are known and thought to be TLR 4 agonists.

Another immunostimulant for use in formulations of the present invention is Quil A and its derivatives. Quil A is a saponin preparation isolated from the South American tree *Quillaja saponaria* Molina and was first described as having adjuvant activity by Dalsgaard et al. in 1974 ("Saponin adjuvants", Archiv. für die gesamte Virusforschung, Vol. 44, Springer Verlag, Berlin, p 243-254). Purified fragments of Quil A have been isolated by HPLC which retain adjuvant activity without the toxicity associated with Quil A (EP 0 362 278), for example QS7 and QS21 (also known as QA7 and QA21). QS-21 is a natural saponin derived from the bark of *Quillaja saponaria* Molina which induces CD8+ cytotoxic T cells (CTLs), Th1 cells and a predominant IgG2a antibody response.

Particular formulations of QS21 have been described which further comprise a sterol (WO 96/33739). The ratio of QS21:sterol will typically be in the order of 1:100 to 1:1 weight to weight. Generally an excess of sterol is present, the ratio of QS21:sterol being at least 1:2 w/w. Typically for human administration QS21 and sterol will be present in a vaccine in the range of about 1 µg to about 100 µg, such as about 10 µg to about 50 µg per dose.

Liposomes generally contain a neutral lipid, for example phosphatidylcholine, which is usually non-crystalline at room temperature, for example egg yolk phosphatidylcholine, dioleoyl phosphatidylcholine or dilauryl phosphatidylcholine. Liposomes may also contain a charged lipid which when QS21 is present may increase the stability of liposome-QS21 structures for liposomes composed of saturated lipids. In these cases the amount of charged lipid is often 1-20% w/w, such as 5-10%. The ratio of sterol to phospholipid is 1-50% (mol/mol), such as 20-25%.

The saponins may be separate in the form of micelles, mixed micelles (generally, but not exclusively with bile salts) or may be in the form of ISCOM matrices (EP 0 109 942), liposomes or related colloidal structures such as worm-like or ring-like multimeric complexes or lipidic/layered structures and lamellae when formulated with cholesterol and lipid, or in the form of an oil in water emulsion (for example as in WO 95/17210).

In one aspect the adjuvant comprises 3D-MPL.
In one aspect the adjuvant comprises QS21.
In one aspect the adjuvant comprises CpG.
In one aspect the adjuvant is formulated as an oil in water emulsion.
In one aspect the adjuvant is formulated as liposomes.

Adjuvants combinations include 3D-MPL and QS21 (EP 0 671 948 B1), oil in water emulsions comprising 3D-MPL and QS21 (WO 95/17210, WO 98/56414), 3D-MPL formulated with other carriers (EP 0 689 454 B1) or 3D-MPL and QS21 in a liposomal formulation. Other suitable adjuvant systems comprise a combination of 3D-MPL, QS21 and a CpG oligonucleotide as described in U.S. Pat. No. 6,558,670 and U.S. Pat. No. 6,544,518.

In one embodiment of the present invention provides:
a pharmaceutical composition, for example as a bulk composition or as individual doses such as one or two doses in the same container, or
a vaccine composition,
comprising a particle as defined herein and wherein the vaccine composition further comprises an adjuvant.

In one aspect the invention provides a composition comprising:
a particle according to the invention, for example in a quantity to correspond 10 to 100 µg per dose,
an alkali metal salt, for example sodium chloride in the range to correspond to 1 to 10 mg per dose,
a phospholipids such as DOPC, for example in a quantity to correspond to the range 100 to 1000 µg per dose, and
optionally cholesterol, for example in a quantity to correspond to the range 10 to 250 µg per dose.

In one aspect the composition further comprises an antioxidant, for example an antioxidant with a thiol functional group such as monothioglycerol, N-acetyl cysteine, cysteine, glutathione or mixtures thereof.

In one aspect each dose or bidose is lyophilized.

A single dose of a vaccine may be provided to a patient in 500 µL of fluid. A vaccine may require making up to final volume with water for injection before use.

Vaccine preparation is generally described in New Trends and Developments in Vaccines, edited by Voller et al., University Park Press, Baltimore, Md., U.S.A., 1978. Encapsulation within liposomes is described, for example, by Fullerton, U.S. Pat. No. 4,235,877.

Quantities

The amount of the protein particles of the invention present in each vaccine dose is selected as an amount which induces an appropriate immune response or a immunoprotective response without significant, adverse side effects in typical vaccines. Such amount will vary depending upon which specific immunogen is employed and whether or not the vaccine is adjuvanted. Generally, it is expected that each does will comprise 1-1000 µg of protein, for example 1-200 µg such as 10-100 µm. An optimal amount for a particular vaccine can be ascertained by standard studies involving observation of antibody titres and other responses in subjects. Following an initial vaccination, subjects may receive a boost in about 4 weeks, followed by for example repeated boosts every six months to twelve months for as long as a risk of infection exists. The immune response to the particles of this invention is thought to be enhanced by the use of adjuvant and or an immunostimulant.

The amount of 3D-MPL used is generally small, but depending on the vaccine formulation may be in the region of 1-1000 µg per dose, for example 1-500 µg per dose, and such as between 1 to 100 µg per dose, in particular 10, 15, 20, 25, 30, 35, 40, 45, 50, 55, 60, 65, 70, 75, 80, 85, or 90 µg per dose.

The amount of CpG or immunostimulatory oligonucleotides in the adjuvants or vaccines of the present invention is generally small, but depending on the vaccine formulation may be in the region of 1-1000 µg per dose, such as 1-500 µg per dose.

The amount of saponin for use in the adjuvants of the present invention may be in the region of 1-1000 µg per dose, particularly 1-500 µg per dose, for example 1-250 µg per dose, and such as in the range 1 to 100 µg per dose in particular 10, 15, 20, 25, 30, 35, 40, 45, 50, 55, 60, 65, 70, 75, 80, 85, or 90 µg per dose The formulations of the present invention may be used for both prophylactic and/or therapeutic, particularly prophylactic purposes. Accordingly the invention provides a vaccine composition as described herein for use in medicine, for example, for the treatment and/or prophylaxis of malaria, including severe malaria.

A further aspect of the invention lies in a method of treating a patient susceptible to *plasmodium* infections by administering an effective amount of a pharmaceutical composition or vaccine as hereinbefore described.

In the context of this specification comprising is to be interpreted as including.

Aspects of the invention comprising a certain element are also intended to extend to separate embodiments consisting or consisting essentially of the relevant elements.

The background section of the present specification is provided for the purpose of putting the invention in context. It is NOT to be taken as an admission that the relevant information is known or that the relevant information constitutes common general knowledge.

The examples below are shown to illustrate the methodology, which may be employed to prepare particles of the invention. The examples may or may not form an aspect of the invention.

EXAMPLES

Example 1

Description of Strain Y1834

The yeast recombinant strain Y1834 may be used to express the fusion protein. It consists of the *Saccharomyces cerevisiae* host strain DC5 transformed with the recombinant expression vector pRIT15546.

DC5 is a laboratory yeast strain (ATCC No: 20820) with the following genotype: leu2-3, leu2-112, his3, can1-11. The double leu-2 mutation permits selection for the uptake and maintenance of the pRIT15546 vector which carries a functional LEU-2 gene copy. Only those cells carrying a vector with a LEU-2 gene can grow when leucine is absent from the growth medium.

The vector pRIT15546 is a yeast episomal expression vector (2µ-based vector) carrying the expression cassette. The recombinant expression is driven by a promoter derived from the yeast TDH3 gene (constitutive expression). The construction of pRIT15546 vector is detailed below.

Construction of pRIT15546 vector.
A synthetic gene, with an appropriate codon usage for yeast expression is constructed and sub-cloned into pUC57 vector. The resulting plasmid pUC57/CSV and the yeast expression vector pGf1-S2 are both restricted with the appropriate enzyme. The vector pGf1-S2 was constructed (at GSK) by a multistep cloning procedure. This vector, which already carries an S expression cassette, allows the construction of fusion genes, as N-terminal in-frame fusion with the S gene of Hepatitis B virus. The final expression vector, after sequence verification, was named pRIT15546 (FIG. 1)

Transformation of strain DC5.
The leu- and his-auxotrophic DC5 strain is transformed with the recombinant plasmid pRIT15546, by using yeast standard protocol. Transformed cells were plated on agar selective plates. One transformant was selected and received the official designation Y1834.

Expression of the Recombinant Protein:
Y1834 is grown, at 30° C., in YNB (Yeast Nitrogen Base available from Kracker Scientific Inc) minimal medium supplemented with 8 µg/ml histidine to an O.D. (620 nm) of 0.5. Then cells are harvested and cellular extracts are prepared.

Extract Preparation:
Cells are resuspended in Breaking Buffer and mechanically disrupted (glass beads). Extract is centrifuged for 15 minutes at 5000 rpm. Supernatant fraction is run on SDS-PAGE 4-20%.
Breaking Buffer: 50 mM phosphate Na buffer (PH: 7.5)
4 mMEDTA
Tween-20 0.5%+
+ proteases inhibitor cocktail (Complete/ROCHE)
Cell concentration: 100 ml culture (OD: 0.5) in 5 ml breaking buffer=concentration of 10 OD unit/ml.
Crude extract clarification: extract centrifuged 15 minutes/5000 rpm
Detection of recombinant protein
Clarified extracts are run on SDS-PAGE 4-20%, proteins transferred to nitrocellulose membrane and subjected to immunostaining
Western blot analysis:
Reagent=Mouse monoclonal antibody anti-S (prepared by GSK Biologicals)-(dilution: 1/500)
Anti-S antibodies which are commercially available may be substituted for those employed in this method. Alternatively anti-CSV antibodies may be employed, for example those known as MR4 available from NIH.

Example 2

Description of Strain Y1835

The yeast recombinant strain Y1835 simultaneously expresses the CSV-S fusion protein and the S antigen. To obtain a strain co-expressing CSV-S and S proteins, the *Saccharomyces cerevisiae* strain Y1295, which already carries five integrated copies of S expression cassettes, was transformed with the recombinant integrative expression vector pRIT15582 (FIG. 3).

The strain Y1295 was constructed at GSK by a multistep transformation procedure. The construction of Y1295 strain is described in WO 93/10152. Strain Y1295 has the following genotype: leu2-3, leu2-112, gall. The leu-2 mutation permits selection for the uptake of pRIT15582-derived linear DNA fragment which carries the CSV-S cassette and the functional LEU2 gene.

The vector pRIT15582 is a yeast integrative expression vector (Ty-based vector) carrying the CSV-S expression cassette. The recombinant expression is driven by a promoter derived from the yeast TDH3 gene (constitutive expression). The construction of pRIT15582 vector is detailed below.

Construction of pRIT15582 Integrative Vector.

The starting material used to construct pRIT15582 vector was the expression plasmid pRIT15546 (FIG. 1). The construction of this plasmid is described in example 1. Digestion of pRIT 15546 with HindIII endonuclease liberates a 3706 bp long DNA fragment corresponding to the complete CSV-S expression cassette (pTDH3+CSV-S+tARG3). This HindIII DNA fragment (after filling with T4 DNA polymerase) was inserted on the Ty-based integrative vector pRIT13144 at the unique SalI cloning site (SalI restricted/T4 treated). The resulting plasmid pRIT15582 contains, in addition to the expression cassette, the yeast LEU2 gene as selective marker (FIG. 3). Digestion of pRIT15582 with XhoI endonuclease liberates a 8500 bp linear fragment shown in FIG. 4 which can be integrated into the yeast genome by homologous recombination of the free ends with resident Ty elements.

Transformation of Strain Y1295.

To obtain a strain expressing both S and CSV-S proteins, strain Y1295 was transformed with the 8500 bp linear XhoI fragment (FIG. 4) with selection for Leu+ colonies. Several integrants containing sets of both expression cassettes present in the genome at various ratio were obtained. One transformant carrying four copies of CSV-S cassettes was selected and given the official designation Y1835.

Expression of the Recombinant Protein:

Y1835 is grown, at 30° C., in YNB (Yeast Nitrogen Base available from Kracker Scientific Inc) minimal medium to an O.D (620 nm) of about 0.5 (0.8). Then cells are harvested and cellular extracts are prepared.

Analysis of Expression Products by Immunoblotting:

Extract Preparation:

Cells are re-suspended in Breaking Buffer and mechanically disrupted (glass beads). Extract is centrifuged for 5-10 minutes at 5000 rpm. Supernatant fraction is run on SDS-PAGE 12.5%.

Breaking Buffer: 50 mM phosphate Na buffer (PH: 7.5)
4 mMEDTA
Tween-20 0.5%+
+ proteases inhibitor cocktail (Complete/ROCHE)

Cell concentration: 100 ml culture (OD: 0.5) in 2.5 ml breaking buffer=concentration of 20 OD unit/ml.

Crude extract clarification: extract centrifuged 5-10 minutes/5000 rpm

Detection of Recombinant Protein

Clarified extracts are run on SDS-PAGE 12.5%, proteins transferred to nitrocellulose membrane and subjected to immunostaining Western blot analysis (FIG. 5):

Reagents: 1/Mouse monoclonal antibody anti-S (prepared by GSK Biologicals)-(dilution: 1/250)

2/Rabbit polyclonal antibody anti-CSV (kindly provided by WRAIR)-dilution 1/20,000.

Anti-S antibodies as well as anti-*P. vivax*/CSP antibodies which are commercially available may be substituted for those employed in this method.

Example 3

The following antigens were evaluated:

1. CSV-S,S: mixed particles made in *Saccharomyces cerevisiae* and composed of a CSV construct (i.e. a hybrid CSV molecule addressing the polymorphism in the repeat region and including the N- & C-terminal parts of the CSV protein. In addition, it contains known T & B epitopes) fused to the S antigen from the hepatitis B virus (CSV-S). In addition, there are free S antigens in these particles.
2. CSV-S: simple particles were uniquely composed of the CSV-S construct described above.

The immunogenicity of these vaccine candidates reconstituted in AS01B was evaluated in mice. Experiments were performed as detailed below.

Mice were injected with:

simple particles (CSV-S) and lipomal adjuvant formulation comprising QS21 & MPL at 0 days, 14 days and 28 days, or mixed particles (CSV-S,S) and lipomal adjuvant formulation comprising QS21 & MPL at 0 days, 14 days and 28 days.

The entities were tested at the following doses:

| CSV-S,S | CSV-S |
|---|---|
| 17 µg | 10 µg |
| 3.5 µg | 2 µg |
| 0.7 µg | 0.4 µg |

These quantities were calculated to provide a corresponding amount of CSV.

The antibody responses were measures 14 days after the second immunisation (14pII) and 14 days post third immunisation (14pIII).

The following read-outs were performed:

Antibody response (ELISA performed on the sera from each individual animals from each group):
measured at 2 timepoints: 14pII & 14pIII
2 serologies measured:
  a) antibody response against CSV
  b) antibody response against HBs
At each timepoint, the data was collected from 4 pools of either 4 to 5 mice each.

The results are shown in FIGS. 7 to 16.

FIG. 7 shows that the same level of antibody response is generated to the CSV element for all doses of mixed particles CSV-S,S.

Example 4

Description of Strain Y1840

Figure 2:
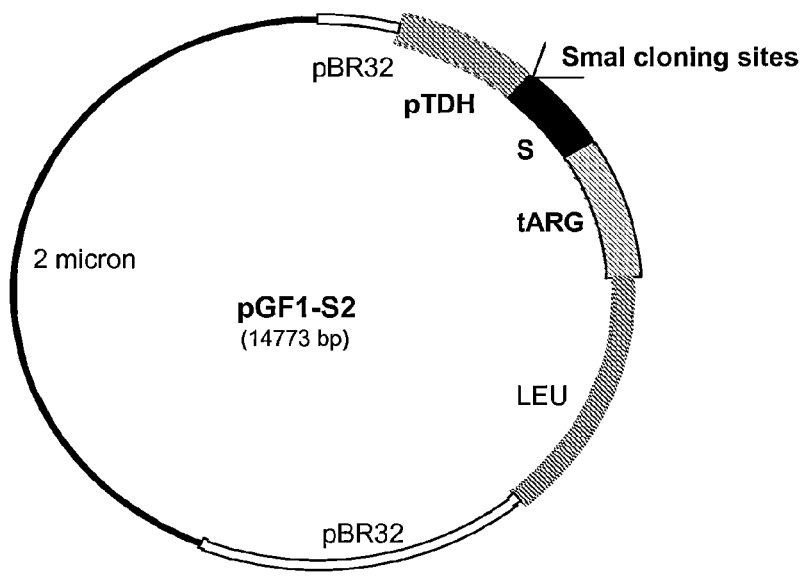
Figure 3:
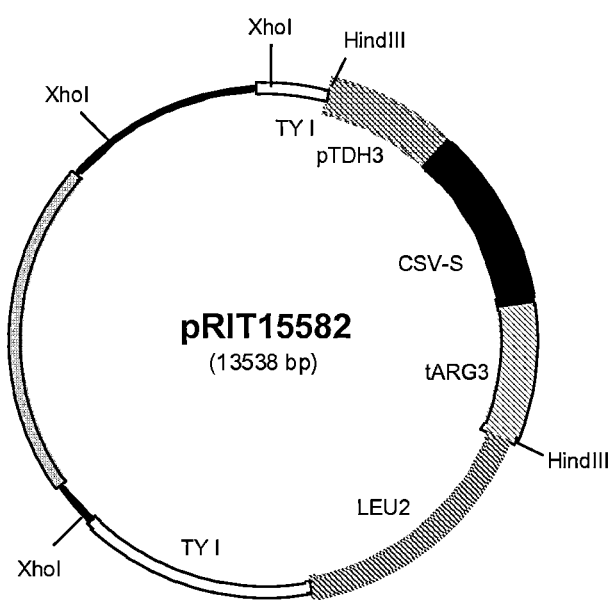
Figure 4:
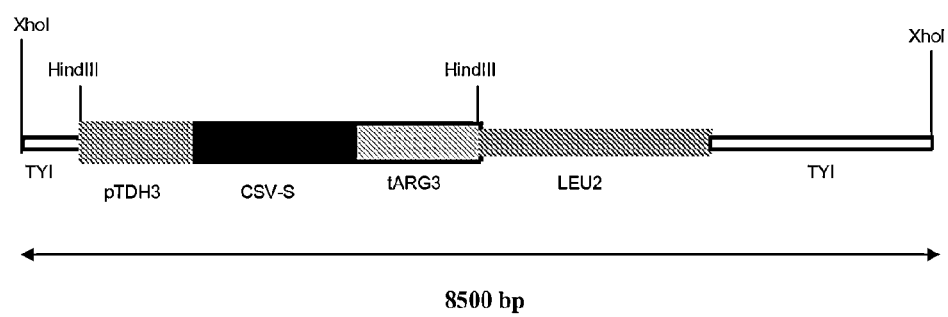
Figure 6:
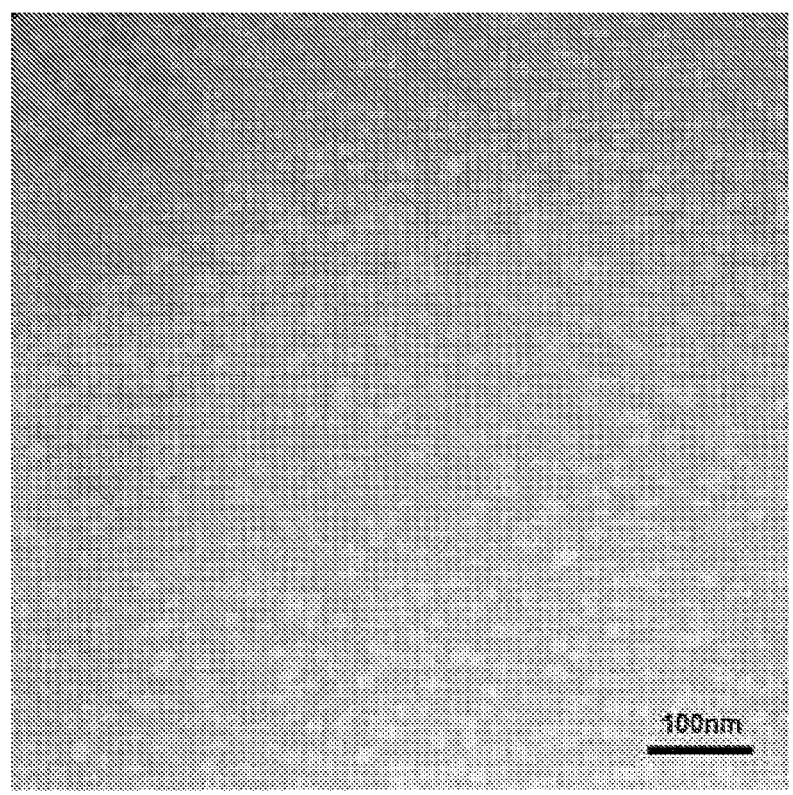
Figure 8:
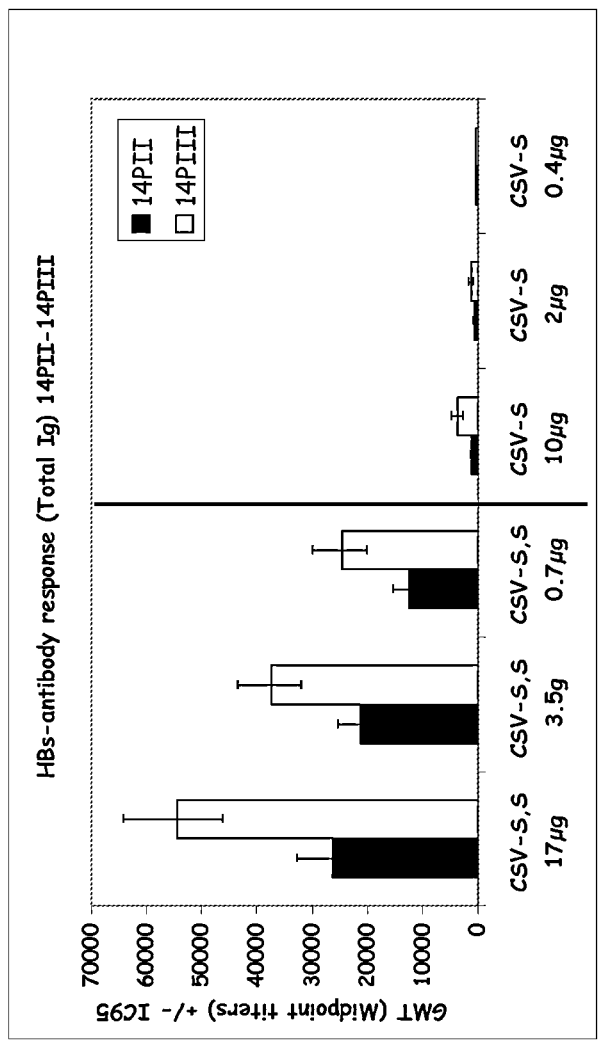
FIG. 8 shows that the immune responses to S antigen in the mixed particle (CSV-S,S) are greater than the responses generated to simple particles (CSV-S).
Figure 9:
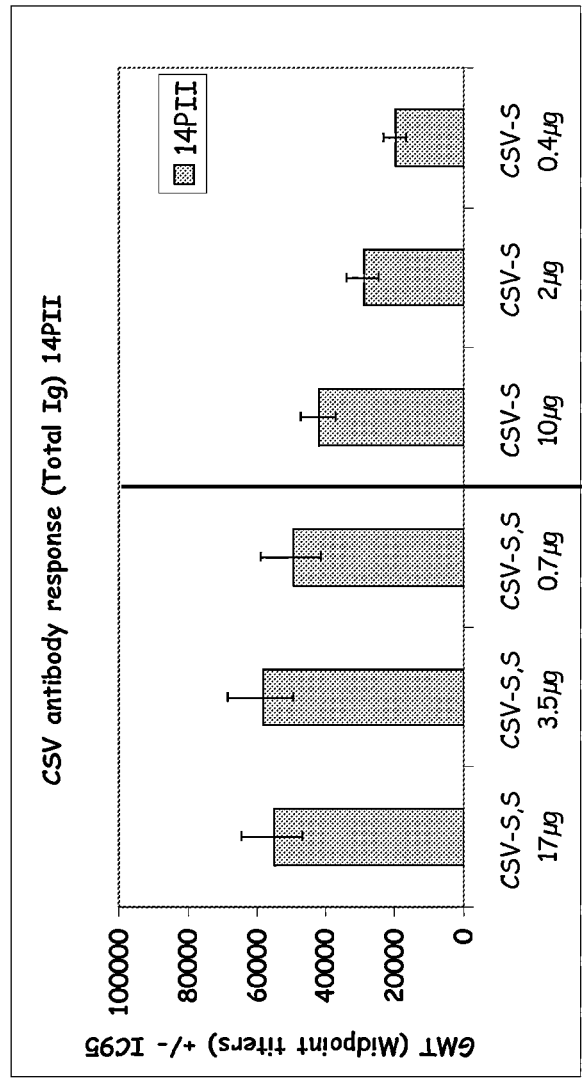
FIG. 9 shows that 14 days post the second immunisation the same level of antibody response to the CSV element is generated for the three doses of CSV-S,S tested. The same trend is observed in FIG. 10, which shows results at 14 days post third injection.
Figure 11:
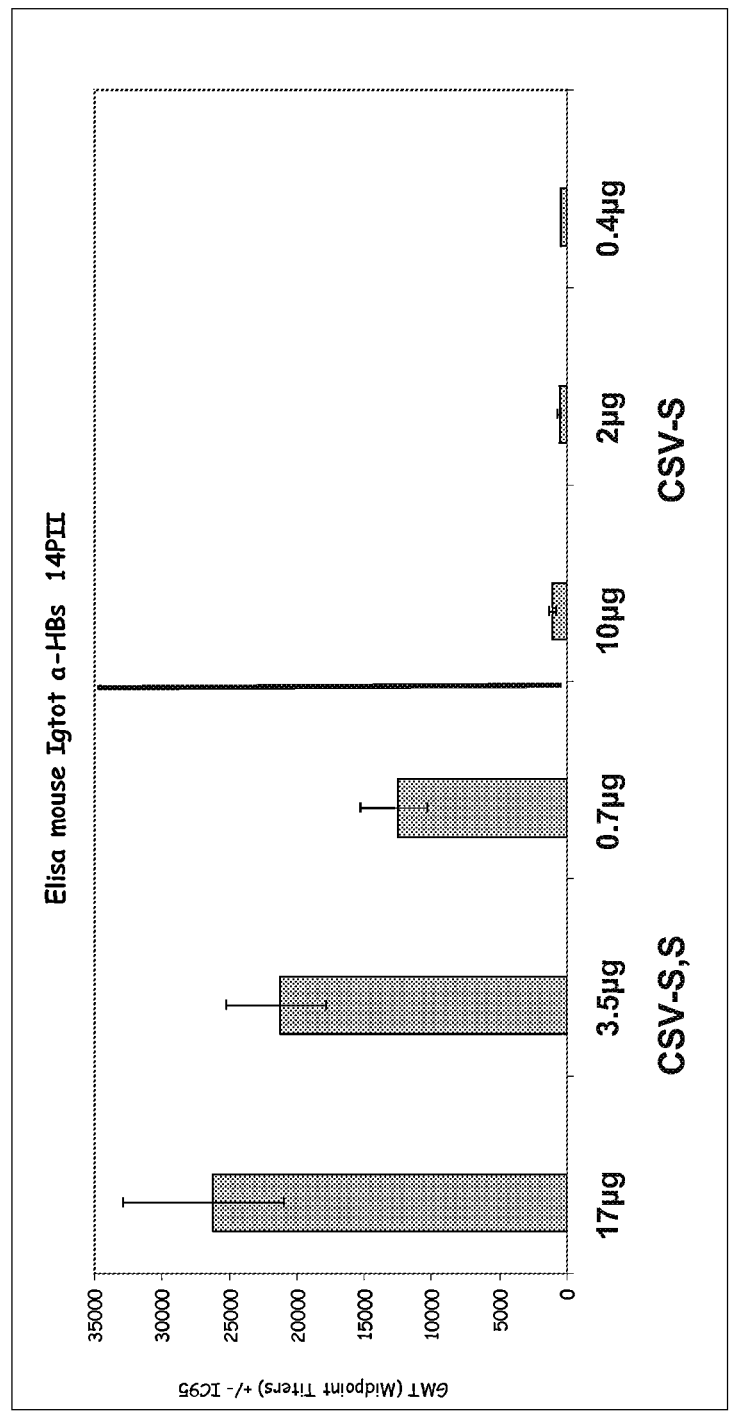
Figure 12:
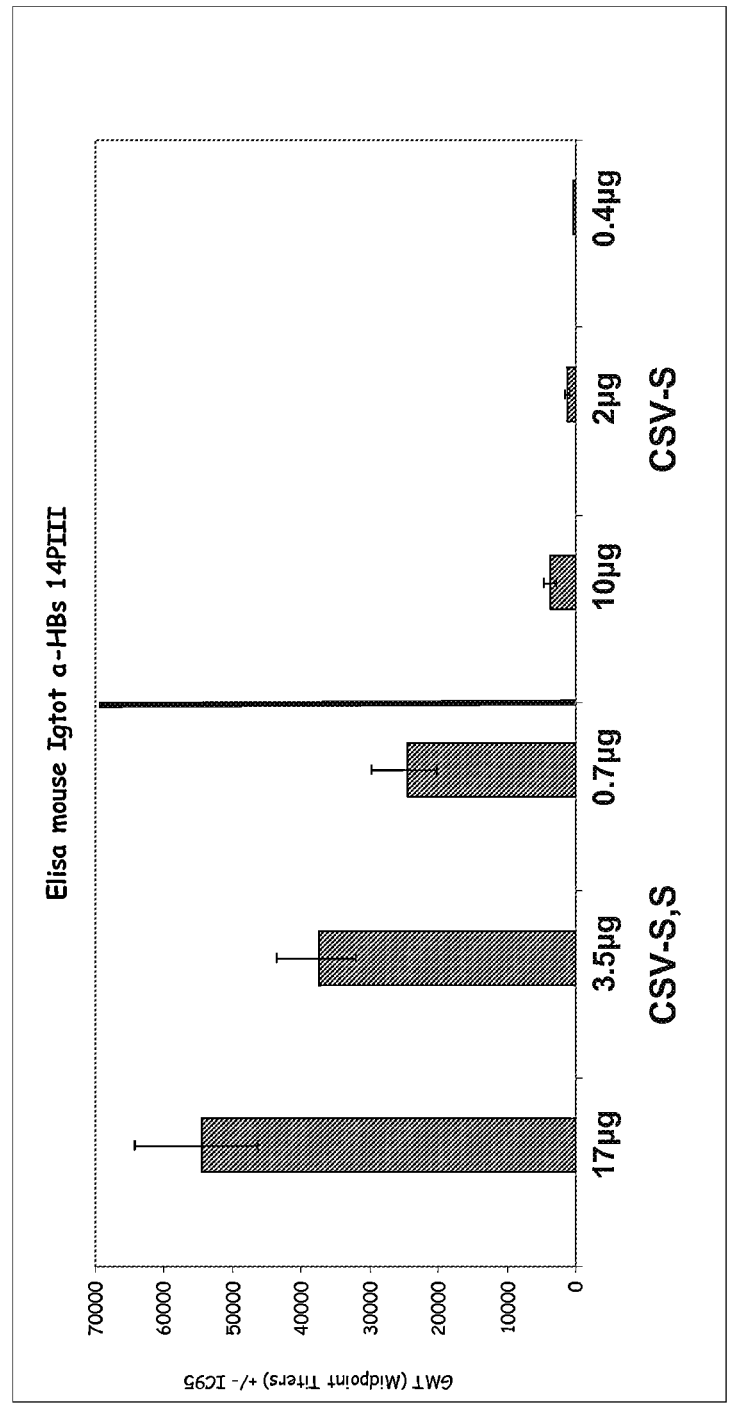
Figure 13:
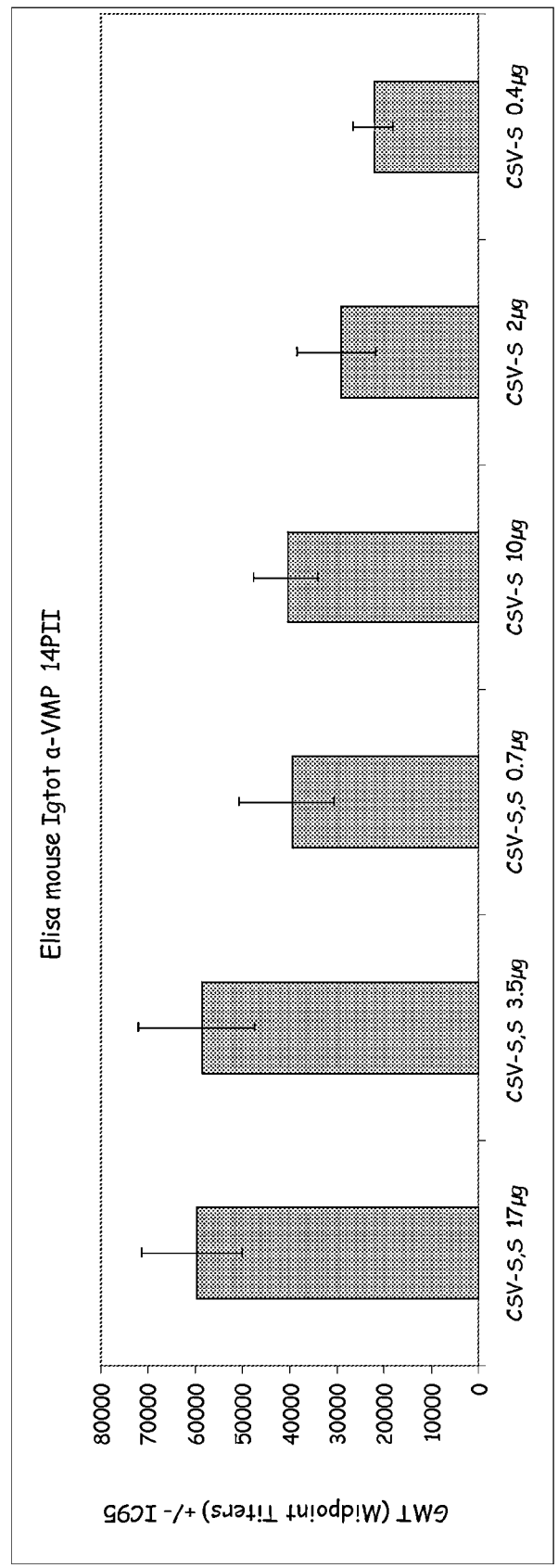
Figure 14:
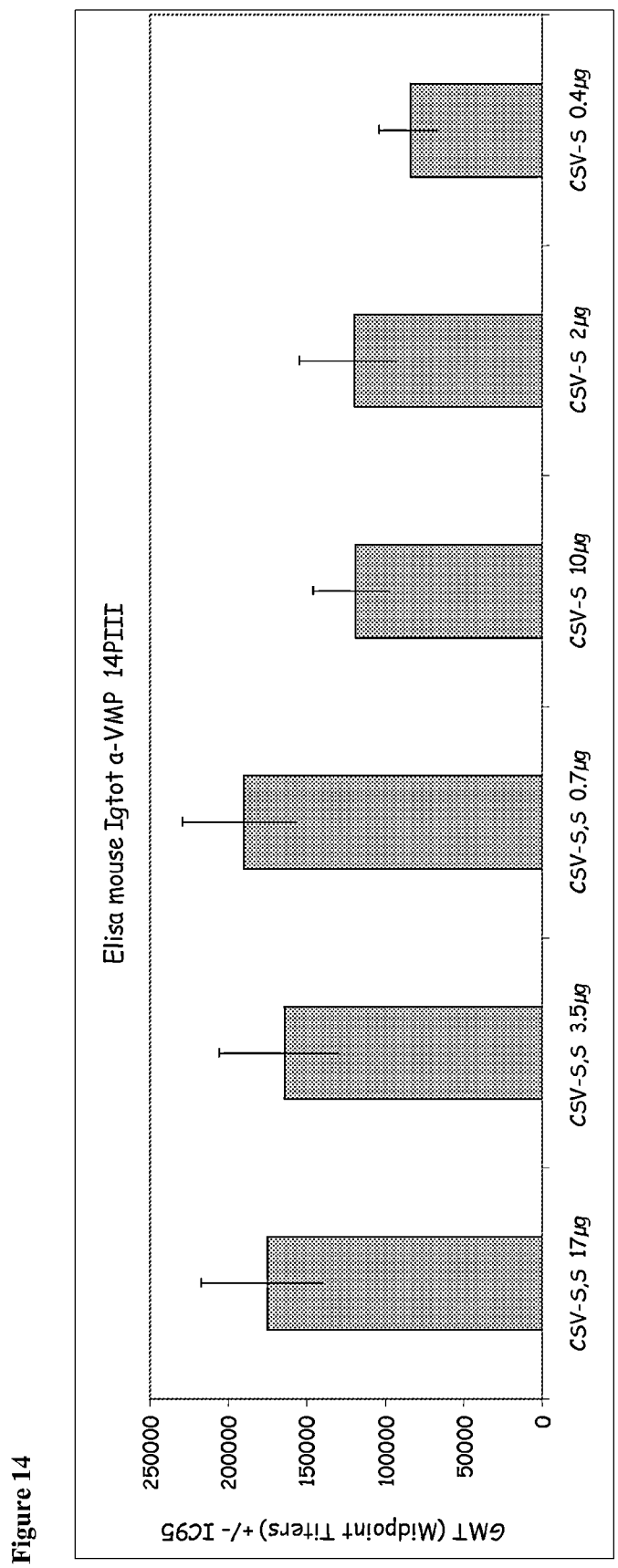
Figure 15:
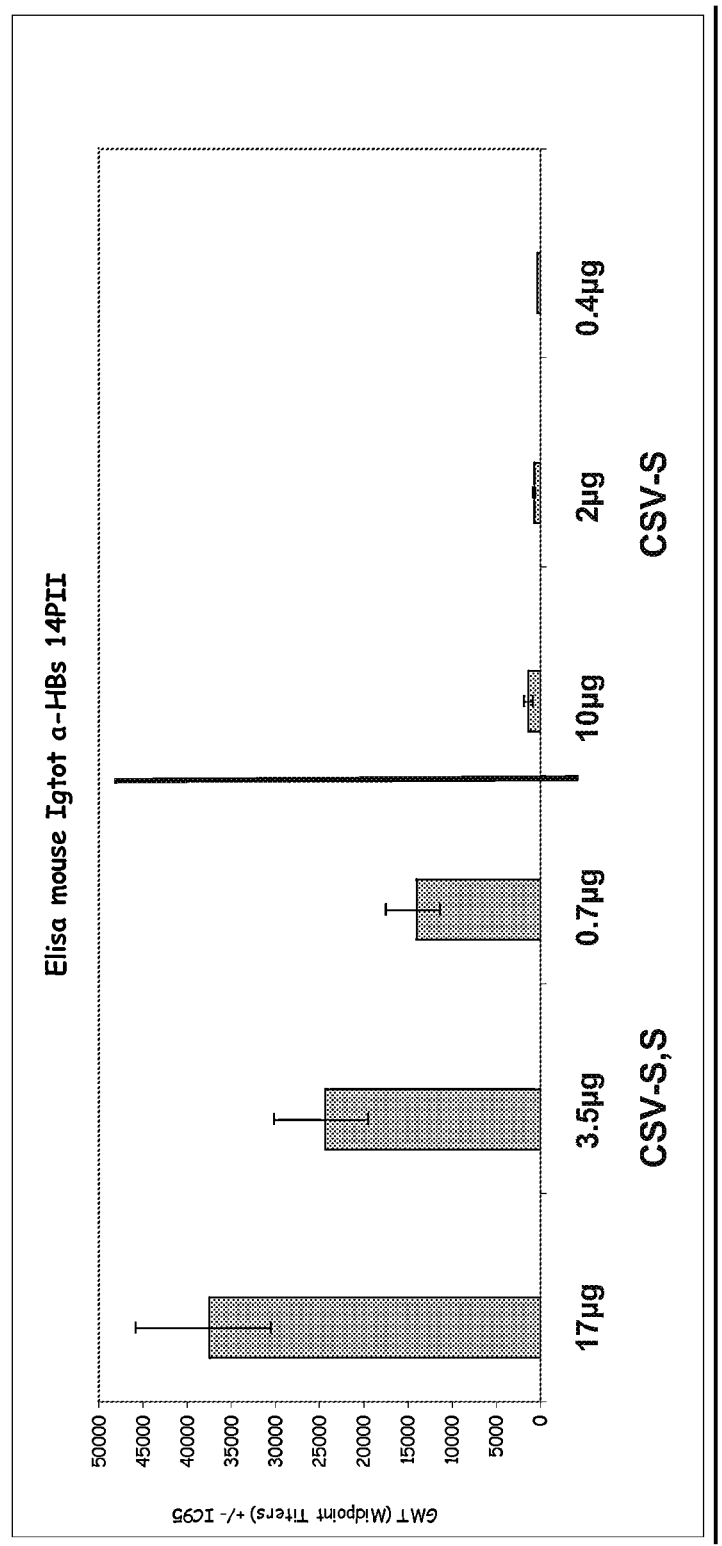
Figure 16:
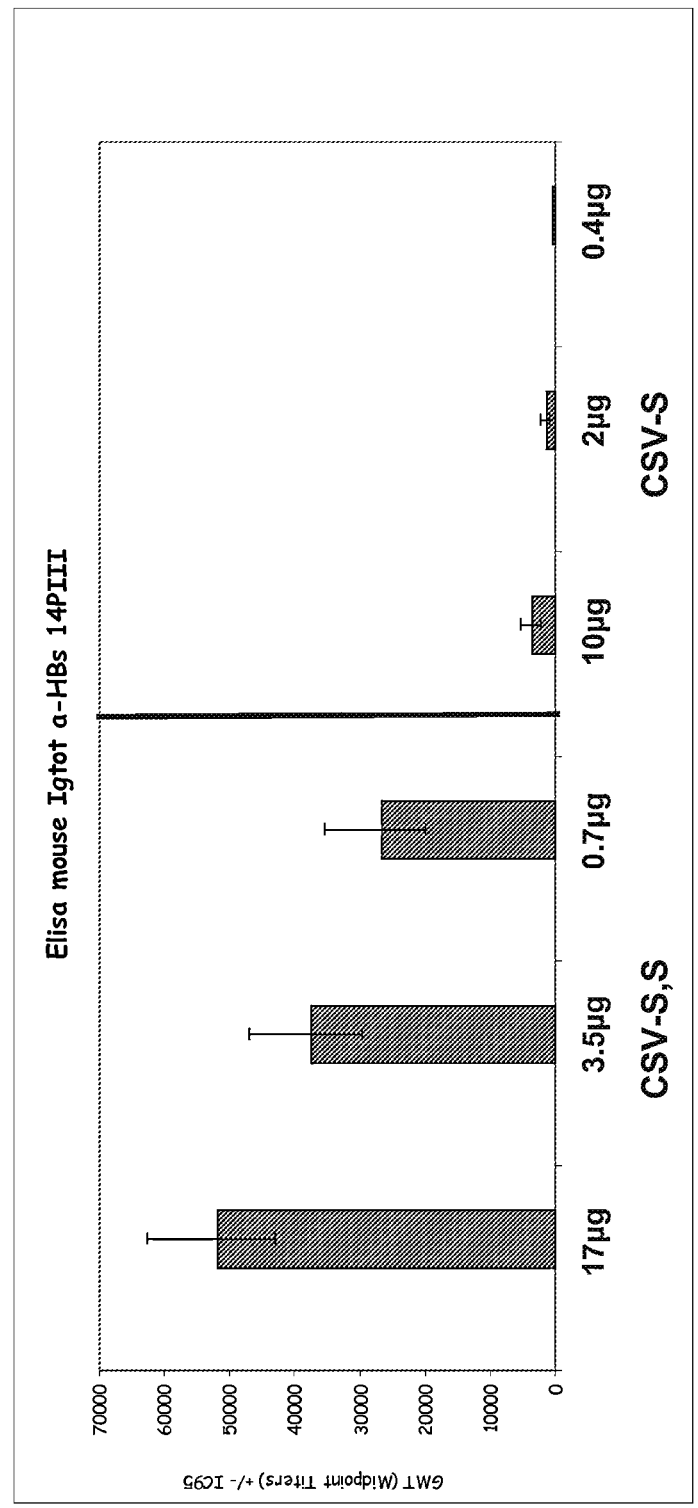
Figure 17:
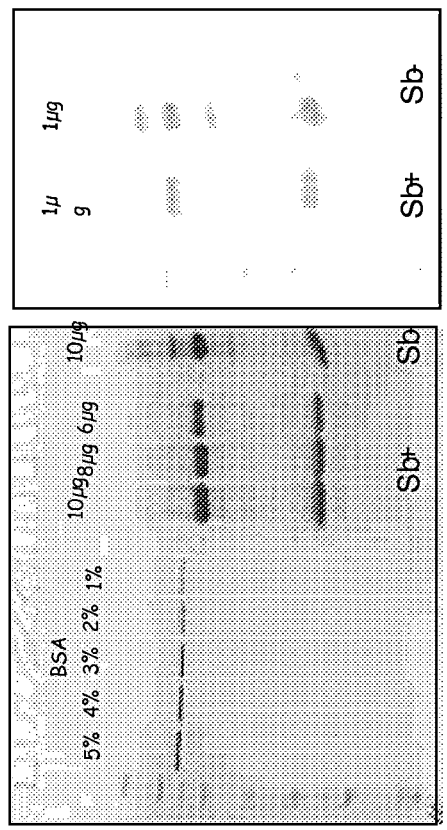
Figure 20:
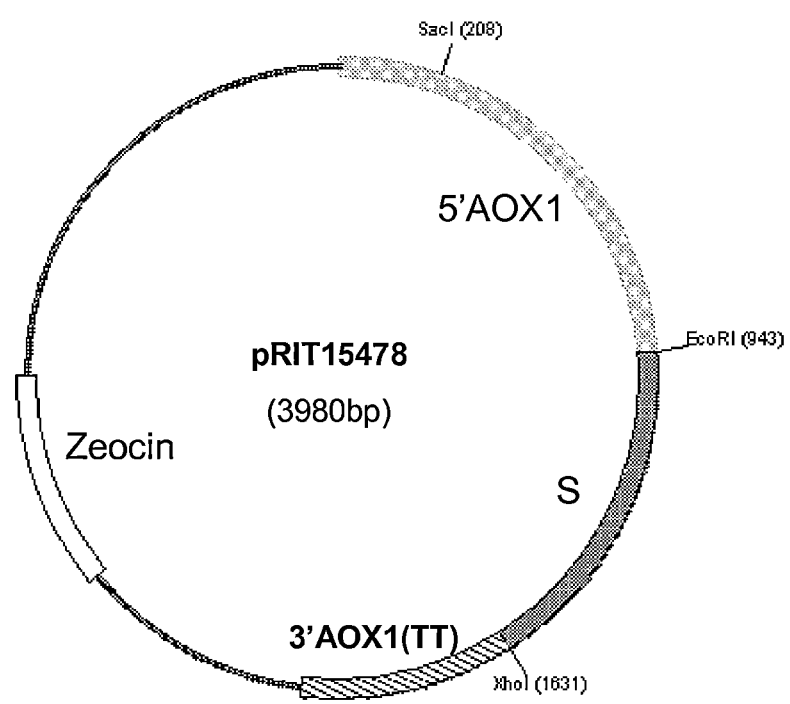
Figure 21:
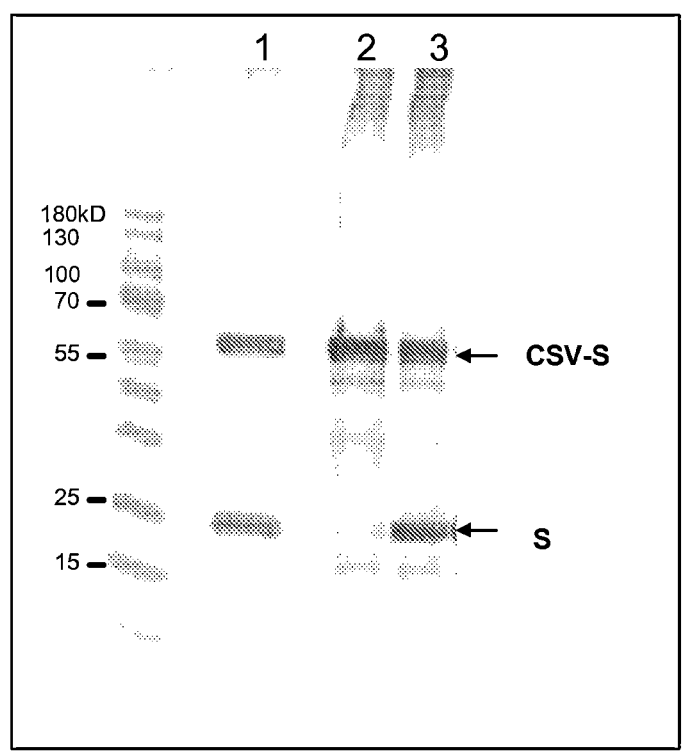

The *Pichia pastoris* strain Y1840 expresses the CSV-S fusion protein. Strain Y1840 contains four copies of the CSV-S fusion gene, integrated in the genome. To obtain a strain expressing the CSV-S fusion protein, the *Pichia pastoris* strain GS115 was transformed with an integrative linear DNA fragment which carries the CSV-S cassette and the functional HIS4 gene.

GS115 is a laboratory yeast strain (ATCC No: 20864) with the following genotype: his4. The his4 mutation permits selection for the uptake of the pRIT15607-derived linear DNA fragment which carries the CSV-S cassette and the functional HIS4 gene.

The vector pRIT15607 is a *Pichia pastoris* integrative expression vector carrying the CSV-S expression cassette. The recombinant expression is driven by the strong, tightly regulated methanol inducible AOX1 promoter. The construction of pRIT15607 vector is detailed below.

Construction of pRIT15607 Vector.
  The CSV-S fusion gene, present on pRIT15546, was amplified by PCR and cloned into the pGEM-T Easy intermediate vector (Promega, cat No: # A1360). After sequence verification the recombinant plasmid was digested with the appropriate restriction enzymes and cloned into the pHIL-D2 *Pichia pastoris* integrative vector. The final expression vector, after sequence verification, was named pRIT15607 (FIG. 18). Digestion of pRIT15607 with NotI endonuclease liberates a 6816 bp linear fragment which can be integrated into the yeast genome by homologous recombination at the resident AOX1 locus.

Transformation of Strain GS115.
  The GS115 host strain was transformed with the recombinant plasmid pRIT15607. Prior to transformation the integrative vector was restricted with NotI in order to release a linear DNA fragment carrying the expression cassette and the HIS4 selective marker. NotI restriction will favor integration at the AOX1 locus. Transformed cells were plated on agar selective plates. Multicopy integrant clones were selected by quantitative dot blot analysis. Among the clones selected has having a high copy number of integrated CSV-S expression cassettes, one of them showing the highest expression level for CSV-S recombinant protein was selected and given the official designation Y1840. This clone carries four copies of the CSV-S fusion gene.

Expression of the Recombinant Protein:
  Y1840 is grown, at 30° C., in YNB (Yeast Nitrogen Base available from Kracker Scientific Inc) minimal medium supplemented with 1% glycerol as a carbon source to an O.D. (620 nm) of about 0.5 (0.709 in this case). Then cells are harvested and resuspended in the same volume of YNB medium supplemented with 1% methanol as a carbon source (as inducer) and incubated at 30° C. for about 16 hours.

Extract Preparation:
Methanol induced cells are centrifuged, cell pellets resuspended in Breaking Buffer and mechanically disrupted (glass beads or French press). Extract is centrifuged for 5-10 minutes at 5000 rpm. Supernatant fraction is run on SDS-PAGE 12.5%.

Breaking Buffer: 60 mM $Na_2HPO_4$
  40 mM $NaH_2PO_4$
  1 mM $MgSO_4$
  10Mm KCl
  Tween-20 0.5%
  2Mm PMSF Cell concentration: 100 ml culture (OD: 0.5) in 2.5 ml breaking buffer=concentration of 20 OD unit/ml.

Crude extract clarification: extract centrifuged 5-10 minutes/5000 rpm

Figure 23:
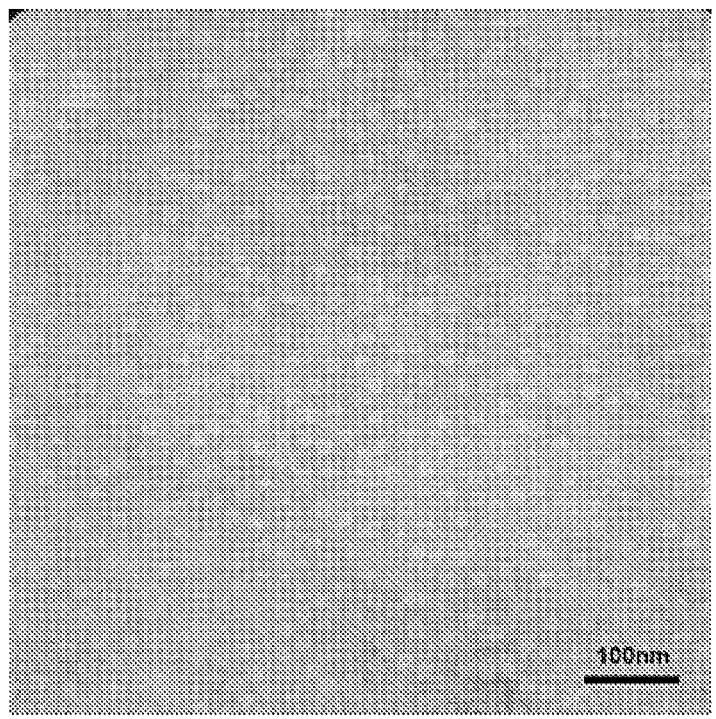
Figure 24:
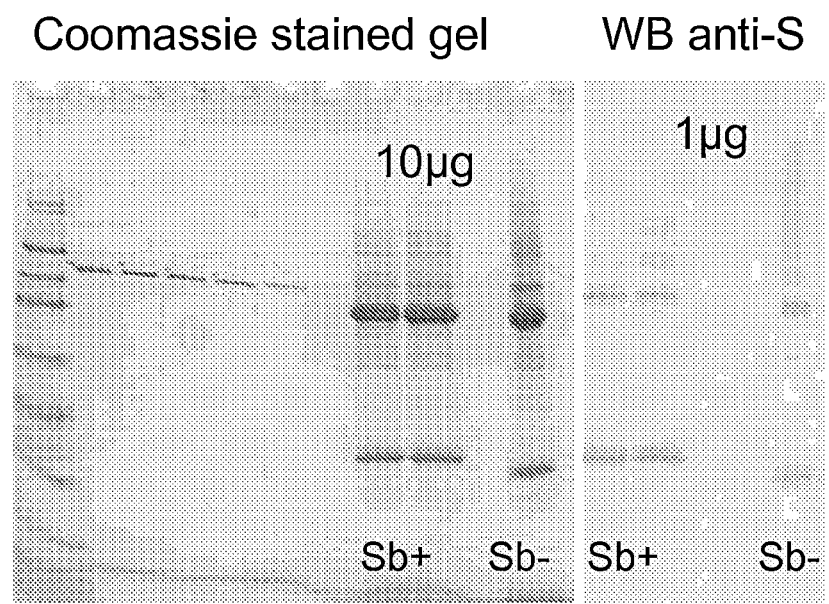

Detection of Recombinant Protein
Clarified extracts are run on SDS-PAGE 12.5%, proteins transferred to nitrocellulose membrane and subjected to immunostaining See FIG. 23.

Western blot analysis:
  Reagent=Mouse monoclonal antibody anti-S (prepared by GSK Biologicals)–(dilution: 1/250)
  Anti-S antibodies which are commercially available may be substituted for those employed in this method. Alternatively anti-CSV antibodies may be employed, for example those known as MR4 available from NIH.

CSV-S fusion protein: MW theoretical: 51762 Daltons
  MW apparent: 55 kDa

Example 5

Description of Strain Y1847

The *Pichia pastoris* strain Y1847 simultaneously expresses the CSV-S fusion protein and the S antigen. To obtain a strain co-expressing CSV-S and S proteins, the *Pichia pastoris* strain Y1840, which already carries four integrated copies of CSV-S expression cassettes, was transformed with the recombinant integrative expression vector pRIT15478.

Construction of strain Y1840 is described above in Example 4

The vector pRIT15478 is the pPICZ-A (Invitrogen, cat No. V 190-20) integrative expression vector carrying the S expression cassette. The recombinant expression is driven by the methanol inducible AOX1 promoter. The construction of pRIT15478 vector is detailed below.

Construction of pRIT15478 integrative vector.

The S gene was amplified by PCR using pRIT15469 recombinant plasmid as template (this plasmid carries the S gene from hepatitis B). The upstream primer (5' GTAACCG GAATTCAATGGAGAACATCACATCAG 3') contains the recognition sequence for EcoRI (underlined) in front of the ATG start codon (in bold). The downstream primer (5'GAAGCTCCG CTCGAGTTAAATGTATACCCAGAGAC 3') contains the recognition sequence for XhoI (underlined) just after the terminal codon (in bold). After digestion with EcoRI and XhoI restriction enzymes, the PCR product was directly inserted into the pPICZ-A vector, between EcoRI and XhoI cloning sites. After verification of the nucleotide sequences of the insert the recombinant plasmid was named pRIT15478. The physical map of pRIT15478 is illustrated in FIG. 18.

Transformation of Strain Y1840.

Prior to transformation, pRIT15478 vector was linearized within the 5' AOX1 region by restriction with SacI. The linearized vector will integrate by gene insertion into the host 5' AOX1 region.

Competent cells of *P. pastoris* strain Y1840 were transformed by electroporation with 10 μg of pRIT 15478 vector, according to Invitrogen's instruction manual. Transformants were plated on agar selective plates containing 100 μg/ml Zeocin. Multicopy integrant clones were selected by quantitative dot blot analysis.

One transformant carrying, in addition of the four CSV-S cassettes already present, five copies of S cassettes was selected and given the official designation Y1847.

Expression of the Recombinant Protein:

Y1847 is grown, at 30° C., in YNB (Yeast Nitrogen Base available from Kracker Scientific Inc) minimal medium supplemented with 1% glycerol to an O.D. (620 nm) of 0.5. Then cells are harvested and resuspended in the same volume of YNB medium supplemented with 1% methanol (as inducer) and incubated at 30° C. for 16 hours. cellular extracts are prepared.

Analysis of Expression Products by Immunoblotting:

Extract Preparation:

Cells are re-suspended in Breaking Buffer and mechanically disrupted (glass beads). Extract is centrifuged for 15 minutes at 5000 rpm. Supernatant fraction is run on SDS-PAGE 12.5%.

Breaking Buffer: 50 mM phosphate Na buffer (PH: 7.5)

4 mMEDTA

Tween-20 0.5%+

+ proteases inhibitor cocktail (Complete/ROCHE)

Cell concentration: 100 ml culture (OD: 0.5) in 2.5 ml breaking buffer=concentration of 20 OD unit/ml.

Crude extract clarification: extract centrifuged 15 minutes/5000 rpm

Detection of Recombinant Protein

Clarified extracts are run on SDS-PAGE 12.5%, proteins transferred to nitrocellulose membrane and subjected to immunostaining Western blot analysis:

Reagents: Mouse monoclonal antibody anti-S (prepared by GSK Biologicals)–(dilution: 1/500)

Anti-S antibodies which are commercially available may be substituted for those employed in this method. Alternatively anti-CSV antibodies may be employed.

CsCl Density Gradient Centrigugation:

The formation of particles in strain Y1847 was analyzed by CsCl density gradient centrifugation. Crude extracts (~20 mg of total protein) was analyzed on a 12 ml 1.5 M CsCl gradient (88 hours at 40.000 rpm, +8° C. in a Beckman 70.1 Ti rotor). Fractions (~0.6 ml) were collected and analyzed by immunoblot using an anti-S antibody. As shown in FIG. 22 western blots CSV-S and S peaks appear at the same fractions (No. 10) of the gradient corresponding to a buoyant density of 1.22 g/cm3. The double (mixed_particle formation is supported by gradient analysis.

REFERENCE (1) Harford N, Cabezon T, Colau B, et al., "Construction and Characterization of a *Saccharomyces Cerevisiae* Strain (RIT4376) Expressing Hepatitis B Surface Antigen", *Postgrad Med J* 63, Supp. 2: 65-70, 1987.

(2) Jacobs E, Rutgers T, Voet P, et al., "Simultaneous Synthesis and Assembly of Various Hepatitis B Surface Proteins in *Saccharomyces cerevisiae", Gene* 80: 279-291, 1989.

(3) Vieira J and Messing J, "The pUC plasmids, an M13mp7-Derived System for Insertion Mutagenesis and Sequencing with Synthetic Universal Primers", *_Gene 19: 259-268, 1982.

(4) Hinnen A, Hicks J B, and Fink G R, "Transformation of Yeast", *Proc Natl Acad Sci USA* 75: 1929-1933, 1980.

(5) Broach J R, Strathern J N, and Hicks J B, "Transformation in Yeast Development of a Hybrid Cloning Vector and Isolation of the CAN 1 Gene", *Gene* 8: 121-133, 1979.

(6) Zhang H, et al., "Double Stranded SDNA Sequencing as a Choice for DNA Sequencing", *Nucleic Acids Research* 16: 1220, 1988.

(7) Dame J B, Williams J L. Mc Cutchan T F, et al., "Structure of the Gene Encoding the Immunodominant Surface Antigen on the Sporozoites of the Human Malaria Parasite *Plasmodium falciparum", Science* 225: 593-599, 1984.

(8) Valenzuela P, Gray P, Quiroga M, et al., "Nucleotide Sequences of the Gene Coding for the Major Protein of Hepatitis B Virus Surface Antigen", *Nature* 280: 815-819, 1979.

(9) In S S, Kee-Hoyung L, Young R K, et al., "comparison of Immunological responses to Various Types of Circumsporozoite Proteins of *Plasmodium vivax* in Malaria Patients of Korea", Microbiol. Immunol. 48(2): 119-123, 2004; Microbiol. Immunol. 2004; 48(2): 119-123.

(10) Rathore D, Sacci J B, de la Vega P, et al., <<"Binding and Invasion of Liver Cells by *Plasmodium falciparum* Sporozoites", J. Biol. Chem. 277(9): 7092-7098, 2002. Rathore et al., 2002, J. Biol. Chem. 277, 7092-8

SEQUENCE LISTING

SEQ ID NO: 1

Pv-CS nucleotide sequence

Acacattgcggacataatgtagatttatctaaagctataaatttaaatggtgtaaacttc aataacgtagacgctagttcactcggggctgcg cacgtaggtcagtctgctagcagggggcgcggtctcggggaaaacccagacgacgaagaa ggtgatgctaaaaagaaaaaggacg gtaaaaaagcggaaccaaaaaatccaagggaaaataaattaaaacagcccggggatcgcg cggatggtcaagcggcgggtaatggg gcggggggtcaaccagcgggggatcgcgcggctggtcagccagcgggggatcgcgcggct ggtcagccagcgggggatggtgc ggctggccaaccagcgggggatcgcgcggatggtcagccagcgggggatcgcgcggatgg tcaaccagccggtgatcgcgcggct ggccaagcggccggtaatggggcgggggtcaagcggccgcgaacggagcggggaaccag ccaggcggcggtaacgctgcga ataaaaaagcggaagatgcgggtggtaacgcgggcggtaatgcgggcggccaaggtcaga acaacgaaggggctaatgcaccaaa cgaaaaatctgtcaaagaatatctcgataaagtccgcgctacagtagggacagaatggac gccatgctctgtaacatgtggtgtcggggt acgcgtgcgccgccgtgtcaatgcggctaacaaaaaaccagaagatctcacgttaaatga tctcgaaacggatgtctgcaca

SEQ ID NO: 2

Amino acid sequence of Pv-CS protein

THCGHNVDLSKAINLNGVNFNNVDASSLGAAHVGQSASRGRGLGEN

PDDEEGDAKKKKDGKKAEPKNPRENKLKQPGDRADGQAAGNGAGG

QPAGDRAAGQPAGDRAAGQPAGDGAAGQPAGDRADGQPAGDRADG

QPAGDRAAGQAAGNGAGGQAAANGAGNQPGGGNAANKKAEDAGG

NAGGNAGGQGQNNEGANAPNEKSVKEYLDKVRATVGTEWTPCSVT

CGVGVRVRRRVNAANKKPEDLTLNDLETDVCT

SEQ ID No 3

CSV HYBRID GENE

ACCCATTGTGGTCACAATGTCGATTTGTCTAAGGCCATTAACTTGAACGGTGTTAATTTC 60

AACAACGTCGATGCTTCTTCTTTAGGTGCCGCTCATGTTGGTCAATCTGCTTCAAGAGGT 120

AGAGGTTTAGGTGAAAACCCAGACGACGAAGAAGGTGACGCTAAGAAGAAGAAGGACGGT 180

AAGAAGGCCGAACCAAAGAACCCAAGAGAAAACAAGTTGAAACAACCAGGTGACAGAGCC 240

GACGGACAAGCAGCTGGTAATGGTGCTGGAGGTCAACCAGCTGGTGACAGAGCTGCCGGT 300

CAGCCTGCTGGTGATAGAGCTGCTGGACAACCTGCTGGAGACGGTGCCGCCGGTCAACCT 360

GCTGGTGATAGAGCAGACGGACAACCAGCTGGTGACCGTGCTGACGGACAGCCAGCCGGC 420

GATAGGGCTGCAGGTCAAGCCGCTGGTAACGGTGCCGGTGGTCAAGCTGCTGCTAACGGT 480

GCTGGTAACCAACCAGGTGGTGGTAACGCTGCCAACAAGAAAGCTGAAGACGCTGGTGGT 540

AATGCTGGAGGTAATGCAGGTGGTCAGGGTCAAAACAACGAAGGTGCTAACGCTCCAAAC 600

GAAAAGTCTGTTAAGGAATACTTAGATAAGGTTAGAGCTACTGTCGGTACTGAATGGACT 660

-continued

CCATGTTCTGTTACTTGTGGTGTCGGTGTTAGAGTTAGAAGAAGAGTTAACGCCGCTAAC 720

AAGAAGCCAGAAGACTTGACTCTAAACGACTTGGAAACTGACGTTTGTACT 771

SEQ ID No 4

CSV-S fusion
Nucleotide sequence
ATGATGGCTCCCGGGACCCATTGTGGTCACAATGTCGATTTGTCTAAGGCCATTAACTTG 60

AACGGTGTTAATTTCAACAACGTCGATGCTTCTTCTTTAGGTGCCGCTCATGTTGGTCAA 120

TCTGCTTCAAGAGGTAGAGGTTTAGGTGAAAACCCAGACGACGAAGAAGGTGACGCTAAG 180

AAGAAGAAGGACGGTAAGAAGGCCGAACCAAAGAACCCAAGAGAAAACAAGTTGAAACAA 240

CCAGGTGACAGAGCCGACGGACAAGCAGCTGGTAATGGTGCTGGAGGTCAACCAGCTGGT 300

GACAGAGCTGCCGGTCAGCCTGCTGGTGATAGAGCTGCTGGACAACCTGCTGGAGACGGT 360

GCCGCCGGTCAACCTGCTGGTGATAGAGCAGACGGACAACCAGCTGGTGACCGTGCTGAC 420

GGACAGCCAGCCGGCGATAGGGCTGCAGGTCAAGCCGCTGGTAACGGTGCCGGTGGTCAA 480

GCTGCTGCTAACGGTGCTGGTAACCAACCAGGTGGTGGTAACGCTGCCAACAAGAAAGCT 540

GAAGACGCTGGTGGTAATGCTGGAGGTAATGCAGGTGGTCAGGGTCAAAACAACGAAGGT 600

GCTAACGCTCCAAACGAAAAGTCTGTTAAGGAATACTTAGATAAGGTTAGAGCTACTGTC 660

GGTACTGAATGGACTCCATGTTCTGTTACTTGTGGTGTCGGTGTTAGAGTTAGAAGAAGA 720

GTTAACGCCGCTAACAAGAAGCCAGAAGACTTGACTCTAAACGACTTGGAAACTGACGTT 780

TGTACTCCCGGGCCTGTGACGAACATGGAGAACATCACATCAGGATTCCTAGGACCCCTG 840

CTCGTGTTACAGGCGGGGTTTTTCTTGTTGACAAGAATCCTCACAATACCGCAGAGTCTA 900

GACTCGTGGTGGACTTCTCTCAATTTTCTAGGGGGATCACCCGTGTGTCTTGGCCAAAAT 960

TCGCAGTCCCCAACCTCCAATCACTCACCAACCTCCTGTCCTCCAATTTGTCCTGGTTAT 1020

CGCTGGATGTGTCTGCGGCGTTTTATCATATTCCTCTTCATCCTGCTGCTATGCCTCATC 1080

TTCTTATTGGTTCTTCTGGATTATCAAGGTATGTTGCCCGTTTGTCCTCTAATTCCAGGA 1140

TCAACAACAACCAATACGGGACCATGCAAAACCTGCACGACTCCTGCTCAAGGCAACTCT 1200

ATGTTTCCCTCATGTTGCTGTACAAAACCTACGGATGGAAATTGCACCTGTATTCCCATC 1260

CCATCGTCCTGGGCTTTCGCAAAATACCTATGGGAGTGGGCCTCAGTCCGTTTCTCTTGG 1320

CTCAGTTTACTAGTGCCATTTGTTCAGTGGTTCGTAGGGCTTTCCCCCACTGTTTGGCTT 1380

TCAGCTATATGGATGATGTGGTATTGGGGGCCAAGTCTGTACAGCATCGTGAGTCCCTTT 1440

ATACCGCTGTTACCAATTTTCTTTTGTCTCTGGGTATACATTTAA 1485

SEQ ID No 5

Amino-Acid sequence
MMAPGTHCGHNVDLSKAINLNGVNFNNVDASSLGAAHVGQSASRGRGLGENPDDEEGDAK 60

KKKDGKKAEPKNPRENKLKQPGDRADGQAAGNGAGGQPAGDRAAGQPAGDRAAGQPAGDG 120

AAGQPAGDRADGQPAGDRADGQPAGDRAAGQAAGNGAGGQAAANGAGNQPGGGNAANKKA 180

EDAGGNAGGNAGGQGQNNEGANAPNEKSVKEYLDKVRATVGTEWTPCSVTCGVGVRVRRR 240

VNAANKKPEDLTLNDLETDVCTPGPVTNMENITSGFLGPLLVLQAGFFLLTRILTIPQSL 300

DSWWTSLNFLGGSPVCLGQNSQSPTSNHSPTSCPPICPGYRWMCLRRFIIFLFILLLCLI 360

FLLVLLDYQGMLPVCPLIPGSTTTNTGPCKTCTTPAQGNSMFPSCCCTKPTDGNCTCIPI 420

PSSWAFAKYLWEWASVRFSWLSLLVPFVQWFVGLSPTVWLSAIWMMWYWGPSLYSIVSPF 480

IPLLPIFFCLWVYI 494

-continued

SEQ ID NO. 6 & 7
Nucelotide sequence of the RTS expression cassette and predicted
translation product of the RTS-HBsAg hybrid protein.
The translation product initiated from the TDH3 ATG codon is
shown below the DNA sequence.

```
AAGCTTACCAGTTCTCACACGGAACACCACTAATGGACACAAATTCGAAATACTTTGACC

CTATTTTCGAGGACCTTGTCACCTTGAGCCCAAGAGAGCCAAGATTTAAATTTTCCTATG

ACTTGATGCAAATTCCCAAAGCTAATAACATGCAAGACACGTACGGTCAAGAAGACATAT

TTGACCTCTTAACTGGTTCAGACGCGACTGCCTCATCAGTAAGACCCGTTGAAAAGAACT

TACCTGAAAAAAACGAATATATACTAGCGTTGAATGTTAGCGTCAACAACAAGAAGTTTA

ATGACGCGGAGGCCAAGGCAAAAAGATTCCTTGATTACGTAAGGGAGTTAGAATCATTTT

GAATAAAAAACACGCTTTTTCAGTTCGAGTTTATCATTATCAATACTGCCATTTCAAAGA

ATACGTAAATAATTAATAGTAGTGATTTTCCTAACTTTATTTAGTCAAAAATTAGCCTTT

TAATTCTGCTGTAACCCGTACATGCCCAAAATAGGGGGCGGGTTACACAGAATATATAAC

ATCGTAGGTGTCTGGGTGAACAGTTTATCCCTGGCATCCACTAAATATAATGGAGCTCGC

TTTTAAGCTGGCATCCAGAAAAAAAAGAATCCCAGCACCAAAATATTGTTTTCTTCACC

AACCATCAGTTCATAGGTCCATTCTCTTAGCGCAACTACAGAGAACAGGGGCACAAACAG

GCAAAAAACGGGCACAACCTCAATGGAGTGATGCAACCTGCCTGGAGTAAATGATGACAC

AAGGCAATTGACCCACGCATGTATCTATCTCATTTTCTTACACCTTCTATTACCTTCTGC

TCTCTCTGATTTGGAAAAAGCTGAAAAAAAAGGTTGAAACCAGTTCCCTGAAATTATTCC

CCTACTTGACTAATAAGTATATAAAGACGGTAGGTATTGATTGTAATTCTGTAAATCTGTAAATCTAT

TTCTTAAACTTCTTAAATTCTACTTTTATAGTTAGTCTTTTTTTAGTTTTAAAACACCA

AGAACTTAGTTTCGAATAAACACACATAAACAAACAAAATGATGGCTCCCGATCCTAATG
                                      MetMetAlaProAspProAsnA

CAAATCCAAATGCAAACCCAAATGCAAACCCAAACGCAAACCCCAATGCAAATCCTAATG
LaAsnProAsnAlaAsnProAsnAlaAsnProAsnAlaAsnProAsnAlaAsnProAsnA

CAAACCCCAATGCAAATCCTAATGCAAATCCTAATGCCAATCCAAATGCAAATCCAAATG
LaAsnProAsnAlaAsnProAsnAlaAsnProAsnAlaAsnProAsnAlaAsnProAsnA

CAAACCCAAACGCAAACCCCAATGCAAATCCTAATGCCAATCCAAATGCAAATCCAAATG
LaAsnProAsnAlaAsnProAsnAlaAsnProAsnAlaAsnProAsnAlaAsnProAsna CAAACCCAAATGCAAACCCAAATGCAAACCCCAATGCAAATCCTAATAAAAACAATCAAG
LaAsnProAsnAlaAsnProAsnAlaAsnProAsnAlaAsnProAsnLysAsnAsnGlnG GTAATGGACAAGGTCACAATATGCCAAATGACCCAAACCGAAATGTAGATGAAAATGCTA
LyAsnGlyGlnGlyHisAsnMetProAs-
nAspProAsnAspProAsnArgAsnValAspGluAsnAlaA ATGCCAACAATGCTGTAAAAAATAATAATAACGAAGAACCAAGTGATAAGCACATAGAAC
snAlaAsnAsnAlaValLysAsnAsnAsnGluGluProSerAspLysHisIleGluG AATATTTAAAGAAAATAAAAAATTCTATTTCAACTGAATGGTCCCCATGTAGTGTAACTT
LnTyrLeuLysLysIleLysAsnSerIleSerThrGluTrpSerProCysSerValThrC GTGGAAATGGTATTCAAGTTAGAATAAAGCCTGGCTCTGCTAATAAACCTAAAGACGAAT
YsGlyAsnGlyIleGlnValArgIleLysProGlySerAlaAsnLysProLysAspGluL TAGATTATGAAAATGATATTGAAAAAAAAATTTGTAAAATGGAAAAGTGCTCGAGTGTGT
euAspTyrGluAsnAspIleGluLysLysIleCysLysMetGluLysCysSerSerValP
```

-continued

```
TTAATGTCGTAAATAGTCGACCTGTGACGAACATGGAGAACATCACATCAGGATTCCTAG
HeAsnValValAsnSerArgProValThrAsnMetGluAsnIleThrSerGlyPheLeuG
GACCCCTGCTCGTGTTACAGGCGGGGTTTTTCTTGTTGACAAGAATCCTCACAATACCGC
LyProLeuLeuValLeuGlnAlaGlyPhePheLeuLeuThrArgIleLeuThrIleProG
AGAGTCTAGACTCGTGGTGGACTTCTCTCAATTTTCTAGGGGGATCACCCGTGTGTCTTG
LnSerLeuAspSerTrpTrpThrSerLeuAsnPheLeuGlyGlySerProValCysLeuG
GCCAAAATTCGCAGTCCCCAACCTCCAATCACTCACCAACCTCCTGTCCTCCAATTTGTC
LyGlnAsnSerGlnSerProThrSerAsnHisSerProThrSerCysProProIleCysP
CTGGTTATCGCTGGATGTGTCTGCGCGTTTTATCATATTCCTCTTCATCCTGCTGCTAT
RoGlyTyrArgTrpMetCysLeuArgArgPheIleIlePheLeuPheIleLeuLeuLeuC
GCCTCATCTTCTTATTGGTTCTTCTGGATTATCAAGGTATGTTGCCCGTTTGTCCTCTAA
YsLeuIlePheLeuLeuValLeuLeuAspTyrGlnGlyMetLeuProValCysProLeuI
TTCCAGGATCAACAACAACCAATACGGGACCATGCAAAACCTGCACGACTCCTGCTCAAG
LeProGlySerThrThrThrAsnThrGlyProCysLysThrCysThrThrProAlaGlnG
GCAACTCTATGTTTCCCTCATGTTGCTGTACAAAACCTACGGATGGAAATTGCACCTGTA
LyAsnSerMetPheProSerCysCysCysThrLysProThrAspGlyAsnCysThrCysI
TTCCCATCCCATCGTCCTGGGCTTTCGCAAAATACCTATGGGAGTGGGCCTCAGTCCGTT
LeProIleProSerSerTrpAlaPheAlaLysTyrLeuTrpGluTrpAlaSerValArgP
TCTCTTGGCTCAGTTTACTAGTGCCATTTGTTCAGTGGTTCGTAGGGCTTTCCCCCACTG
HeSerTrpLeuSerLeuLeuValProPheValGlnTrpPheValGlyLeuSerProThrV
TTTGGCTTTCAGCTATATGGATGATGTGGTATTGGGGGCCAAGTCTGTACAGCATCGTGA
AlTrpLeuSerAlaIleTrpMetMetTrpTyrTrpGlyProSerLeuTyrSerIleValS
GTCCCTTTATACCGCTGTTACCAATTTTCTTTTGTCTCTGGGTATACATTTAACGAATTC
ErProPheIleProLeuLeuProIlePhePheCysLeuTrpValTyrIle
CAAGCTGAAACAATTCAAAGGTTTTCAAATCAATCAAGAACTTGTCTCTGTGGCTGATCC
AAACTACAAATTTATGCATTGTCTGCCAAGACATCAAGAAGAAGTTAGTGATGATGTCTT
TTATGGAGAGCATTCCATAGTCTTTGAAGAAGCAGAAAACAGATTATATGCAGCTATGTC
TGCCATTGATATCTTTGTTAATAATAAAGGTAATTTCAAGGACTTGAAATAATCCTTCTT
TCGTGTTCTTAATAACTAATATATAAATACAGATATAGATGCATGAATAATGATATACAT
TGATTATTTTGCAATGTCAATTAAAAAAAAAAAATGTTAGTAAAACTATGTTACATTCCA
AGCAAATAAAGCACTTGGTTAAACGAAATTAACGTTTTTAAGACAGCCAGACCGCGGTCT
AAAAATTTAAATATACACTGCCAACAAATTCCTTCGAGTTGTCCAATTTCACCACTTTTA
TATTTTCATCAACTTCAGCAGATTCAACCTTCTCACATAGAACATTGGAATAAACAGCCT
TAACACCACTTTCAAGTTTGCACAGCGTAATATGAGGAATTTTGTTTTGACAACACAACC
CTTTAATTTTCTCATTGTTTTCATCAATTATGCATCCATCTTTATCTTTAGACAGTTCCA
CTACAATAGCAATAGTTTTTTCATCCCAACATAGTTTTTCGAGCCTAAAATTCAGTTTGT
CGGTCGTTTACCTGCGTATTTTGGTTATTACCAGAGCCTTGTGCATTTTCTATGCGGT
TGTTATTGTACTCCGTTATCTGGTCAGTGTATCTGTTACAATATGATTCCACAACTTTTT
TGCCTCTTTTTCACGGGACGACATGACATGACCTAATGTTATATGAAGTTCCTTCTGAAC
TTTTCCACTAGCTAGTAAATGCTTGAATTTCTCAGTCAGCTCTGCATCGCTAGCAATACA
CCTCTTGACCAATCAATAATTTCATCGTAGTTTTCTATTTAGCTGAGATATATGTAGGT
```

-continued

TTAATTAACTTAGCGTTTTTTGTTGATTATTGTTGCCTTTACCAACTATTTTTCTCACAG

TAGGTTTGTAATCTAAGCTTCCTTCTGAACGCTGTCTCAATTTCATCATCTTTCGGGATCT

CTGGTACCAAAATTGGATAAGCTT

| | SEQ ID No 8 |
|---|---|
| Nucleotide sequence CSV-S fusion gene (cloned into pHIL-D2 integrative *Pichia pastoris* expression vector) | |
| ATGATGGCTCCCGGGACCCATTGTGGTCACAATGTCGATTTGTCTAAGGCCATTAACTTG | 60 |
| AACGGTGTTAATTTCAACAACGTCGATGCTTCTTCTTTAGGTGCCGCTCATGTTGGTCAA | 120 |
| TCTGCTTCAAGAGGTAGAGGTTTAGGTGAAAACCCAGACGACGAAGAAGGTGACGCTAAG | 180 |
| AAGAAGAAGGACGGTAAGAAGGCCGAACCAAAGAACCCAAGAGAAAACAAGTTGAAACAA | 240 |
| CCAGGTGACAGAGCCGACGGACAAGCAGCTGGTAATGGTGCTGGAGGTCAACCAGCTGGT | 300 |
| GACAGAGCTGCCGGTCAGCCTGCTGGTGATAGAGCTGCTGGACAACCTGCTGGAGACGGT | 360 |
| GCCGCCGGTCAACCTGCTGGTGATAGAGCAGACGGACAACCAGCTGGTGACCGTGCTGAC | 420 |
| GGACAGCCAGCCGGCGATAGGGCTGCAGGTCAAGCCGCTGGTAACGGTGCCGGTGGTCAA | 480 |
| GCTGCTGCTAACGGTGCTGGTAACCAACCAGGTGGTGGTAACGCTGCCAACAAGAAAGCT | 540 |
| GAAGACGCTGGTGGTAATGCTGGAGGTAATGCAGGTGGTCAGGGTCAAAACAACGAAGGT | 600 |
| GCTAACGCTCCAAACGAAAAGTCTGTTAAGGAATACTTAGATAAGGTTAGAGCTACTGTC | 660 |
| GGTACTGAATGGACTCCATGTTCTGTTACTTGTGGTGTCGGTGTTAGAGTTAGAAGAAGA | 720 |
| GTTAACGCCGCTAACAAGAAGCCAGAAGACTTGACTCTAAACGACTTGGAAACTGACGTT | 780 |
| TGTACTCCCGGGCCTGTGACGAACATGGAGAACATCACATCAGGATTCCTAGGACCCCTG | 840 |
| CTCGTGTTACAGGCGGGGTTTTCTTGTTGACAAGAATCCTCACAATACCGCAGAGTCTA | 900 |
| GACTCGTGGTGGACTTCTCTCAATTTTCTAGGGGATCACCCGTGTGTCTTGGCCAAAAT | 960 |
| TCGCAGTCCCCAACCTCCAATCACTCACCAACCTCCTGTCCTCCAATTTGTCCTGGTTAT | 1020 |
| CGCTGGATGTGTCTGCGGCGTTTTATCATATTCCTCTTCATCCTGCTGCTATGCCTCATC | 1080 |
| TTCTTATTGGTTCTTCTGGATTATCAAGGTATGTTGCCCGTTTGTCCTCTAATTCCAGGA | 1140 |
| TCAACAACAACCAATACGGGACCATGCAAAACCTGCACGACTCCTGCTCAAGGCAACTCT | 1200 |
| ATGTTTCCCTCATGTTGCTGTACAAAACCTACGGATGGAAATTGCACCTGTATTCCCATC | 1260 |
| CCATCGTCCTGGGCTTTCGCAAAATACCTATGGGAGTGGGCCTCAGTCCGTTTCTCTTGG | 1320 |
| CTCAGTTTACTAGTGCCATTTGTTCAGTGGTTCGTAGGGCTTTCCCCCACTGTTTGGCTT | 1380 |
| TCAGCTATATGGATGATGTGGTATTGGGGGCCAAGTCTGTACAGCATCGTGAGTCCCTTT | 1440 |
| ATACCGCTGTTACCAATTTTCTTTTGTCTCTGGGTATACATTTAA | 1485 |

| | SEQ ID No 9 |
|---|---|
| Amino-Acid sequence CSV-S fusion protein expressed in *Pichia pastoris*. | |
| [MMAPG]THCGHNVDLSKAINLNGVNFNNVDASSLGAAHVGQSASRGRGLGENPDDEEGDAK | 60 |
| KKKDGKKAEPKNPRENKLKQPGDRADGQAAGNGAGGQPAGDRAAGQPAGDRAAGQPAGDG | 120 |
| AAGQPAGDRADGQPAGDRADGQPAGDRAAGQAAGNGAGGQAAANGAGNQPGGGNAANKKA | 180 |
| EDAGGNAGGNAGGQGQNNEGANAPNEKSVKEYLDKVRATVGTEWTPCSVTCGVGVRVRRR | 240 |
| VNAANKKPEDLTLNDLETDVCT[PGPVTN]MENITSGFLGPLLVLQAGFFLLTRILTIPQSL | 300 |
| DSWWTSLNFLGGSPVCLGQNSQSPTSNHSPTSCPPICPGYRWMCLRRFIIFLFILLLCLI | 360 |
| FLLVLLDYQGMLPVCPLIPGSTTTNTGPCKTCTTPAQGNSMFPSCCCTKPTDGNCTCIPI | 420 |
| PSSWAFAKYLWEWASVRFSWLSLLVPFVQWFVGLSPTVWLSAIWMMWYWGPSLYSIVSPF | 480 |
| IPLLPIFFCLWVYI | 494 |

SEQ ID No 10
Nucleotide sequence S gene (cloned into pPICZ-A integrative
Pichia pastoris vector)
ATGGAGAACATCACATCAGGATTCCTAGGACCCCTGCTCGTGTTACAGGC                50

GGGGTTTTCTTGTTGACAAGAATCCTCACAATACCGCAGAGTCTAGACT                 100

CGTGGTGGACTTCTCTCAATTTTCTAGGGGGATCACCCGTGTGTCTTGGC                150

CAAAATTCGCAGTCCCCAACCTCCAATCACTCACCAACCTCCTGTCCTCC                200

AATTTGTCCTGGTTATCGCTGGATGTGTCTGCGGCGTTTTATCATATTCC                250

TCTTCATCCTGCTGCTATGCCTCATCTTCTTATTGGTTCTTCTGGATTAT                300

CAAGGTATGTTGCCCGTTTGTCCTCTAATTCCAGGATCAACAACAACCAA                350

TACGGGACCATGCAAAACCTGCACGACTCCTGCTCAAGGCAACTCTATGT                400

TTCCCTCATGTTGCTGTACAAAACCTACGGATGGAAATTGCACCTGTATT                450

CCCATCCCATCGTCCTGGGCTTTCGCAAAATACCTATGGGAGTGGGCCTC                500

AGTCCGTTTCTCTTGGCTCAGTTTACTAGTGCCATTTGTTCAGTGGTTCG                550

TAGGGCTTTCCCCCACTGTTTGGCTTTCAGCTATATGGATGATGTGGTAT                600

TGGGGGCCAAGTCTGTACAGCATCGTGAGTCCCTTTATACCGCTGTTACC                650

AATTTTCTTTTGTCTCTGGGTATACATTTAA                                   681

Seq ID No 11
Amino Acid sequence S protein
MENITSGFLGPLLVLQAGFFLLTRILTIPQSLDSWWTSLNFLGGSPVCLG                 50

QNSQSPTSNHSPTSCPPICPGYRWMCLRRFIIFLFILLLCLIFLLVLLDY                 100

QGMLPVCPLIPGSTTTNTGPCKTCTTPAQGNSMFPSCCCTKPTDGNCTCI                 150

PIPSSWAFAKYLWEWASVRFSWLSLLVPFVQWFVGLSPTVWLSAIWMMWY                 200

WGPSLYSIVSPFIPLLPIFFCLWVYI                                         226

---

The invention claimed is:

1. An immunogenic protein particle comprising the following monomers:
   a. a fusion protein comprising an antigenic *P. vivax* CS amino acid sequence of SEQ ID NO: 5 and the S antigen of Hepatitis B (CSV-S), and
   b. S antigen from Hepatitis B virus,
wherein the ratio of S to CSV-S is 0.68 to 0.80 as measured by the density of each monomer.

2. The immunogenic particle of claim 1, wherein the ratio is 0.73.

3. The immunogenic particle of claim 1, wherein the CSV-S component has the amino acid sequence shown in Seq ID No: 5.

4. The immunogenic protein particle of claim 1, wherein the antigenic *P. vivax* CS amino acid sequence of SEQ ID NO: 5 comprises at least one repeat unit obtained from the central repeat section of a type I circumsporozoite protein of *P. vivax*.

5. The immunogenic protein particle of claim 1, wherein the antigenic *P. vivax* CS amino acid sequence of SEQ ID NO: 5 comprises at least one repeat unit obtained from the central repeat section of a type II circumsporozoite protein of *P. vivax*.

6. The immunogenic protein particle of claim 1, wherein the antigenic *P. vivax* CS amino acid sequence of SEQ ID NO: 5 comprises SEQ ID NO: 2.

7. A pharmaceutical composition comprising the immunogenic particle of claim 1 and an excipient.

8. The pharmaceutical composition according to claim 7, wherein the excipient is an adjuvant.

9. The pharmaceutical composition according to claim 8, wherein the adjuvant comprises a saponin.

10. The pharmaceutical composition according to claim 9, wherein the saponin is QS21.

11. The pharmaceutical composition according to claim 8, wherein the adjuvant comprises 3-deacylated monophosphoryl lipid A (3D-MPL).

12. The pharmaceutical composition according to claim 11, wherein the 3D-MPL is present as small particle MPL.

13. The pharmaceutical composition according to claim 8, wherein the adjuvant is a liposomal formulation or an oil in water emulsion.

14. The pharmaceutical composition according to claim 7 comprising:
   (a) 10 to 100 μg per dose of said immunogenic particle,
   (b) 1 to 10 mg per dose of an alkali metal salt,
   (c) 100 to 1000 μg per dose of a phospholipid, and
   (d) optionally 10 to 250 μg per dose of cholesterol.

15. The pharmaceutical composition according to claim 7, wherein the composition is a vaccine for parental use.

* * * * *